United States Patent
Levanon et al.

(10) Patent No.: US 10,617,697 B2
(45) Date of Patent: Apr. 14, 2020

(54) EXTRACTS OF EDIBLE FUNGI ENRICHED IN VITAMIN D AND COMPOSTIONS THEREOF AND THEIR USE IN THE TREATMENT OF IMMUNE-RELATED DISORDERS

(71) Applicants: GAVISH-GALILEE BIO APPLICATIONS LTD, Kiryat Shmona (IL); HADASIT MEDICAL RESEARCH SERVICES & DEVELOPMENT LTD, Jerusalem (IL)

(72) Inventors: Dan Levanon, Kfar Blum (IL); Yaron Ilan, Kfar Tavor (IL); Ofer Danai, Mitzpeh Hila (IL)

(73) Assignees: GAVISH-GALILEE BIO APPLICATIONS, LTD., Kiryat Shmona (IL); HADASIT MEDICAL RESEARCH SERVICES & DEVELOPMENT LTD, Jerusalem (IL)

( * ) Notice: Subject to any disclaimer, the term of this patent is extended or adjusted under 35 U.S.C. 154(b) by 0 days.

(21) Appl. No.: 15/544,333

(22) PCT Filed: Jan. 17, 2016

(86) PCT No.: PCT/IL2016/050053
§ 371 (c)(1),
(2) Date: Jul. 18, 2017

(87) PCT Pub. No.: WO2016/113744
PCT Pub. Date: Jul. 21, 2016

(65) Prior Publication Data
US 2018/0008617 A1    Jan. 11, 2018

Related U.S. Application Data

(60) Provisional application No. 62/104,763, filed on Jan. 18, 2015.

(51) Int. Cl.
| | | |
|---|---|---|
| A61K 39/00 | (2006.01) | |
| A01N 63/00 | (2020.01) | |
| A61K 49/00 | (2006.01) | |
| A61K 31/592 | (2006.01) | |
| A61K 36/07 | (2006.01) | |

(52) U.S. Cl.
CPC ............ *A61K 31/592* (2013.01); *A61K 36/07* (2013.01); *A61K 2236/00* (2013.01); *A61K 2236/33* (2013.01); *A61K 2236/331* (2013.01)

(58) Field of Classification Search
CPC .... A61K 39/00; A61K 39/0002; A61K 41/00; A61K 41/0019
USPC .............. 424/9.1, 9.2, 93.5, 274.1
See application file for complete search history.

(56) References Cited

U.S. PATENT DOCUMENTS

| 8,545,915 B2 | 10/2013 | Schroeder |
| 2011/0091579 A1 | 4/2011 | Hausman |
| 2012/0128711 A1 | 5/2012 | Hausman et al. |

FOREIGN PATENT DOCUMENTS

| CA | 2759246 A1 | 10/2009 |
| DE | 202010016402 U1 | 2/2011 |
| WO | 2006007848 A2 | 1/2006 |

OTHER PUBLICATIONS

Babu, U.S., et al., Vitamin D2 from UVB light exposed mushrooms modulates immune response to LPS in rats , Molecular Nutrition Food Research, First Published: Aug. 28, 2013 vol. 58, pp. 318-328.*
International Preliminary Report on Patentability dated Jul. 18, 2017, from International Application No. PCT/IL2016/050053, 10 pages.
Babu, Uma S, et al. "Vitamin D2 from UVB light exposed mushrooms modulates immune response to LPS in rats". Mol Nutr Food Res. 58(2); pp. 318-328. (2014).
Lim, Wee-Chian et al. "Mechanisms of Disease: vitamin D and inflammatory bowel disease". Nature Clinical Practice Gastroenterology and Hepatology vol. 2, No. 7, pp. 308-315 (2005).
Jose, N. et al. "Methanol Extract of the Oyster Mushroom, Pleurotus florida, Inhibits Inflammation and Platelet Aggregation". Phytotherapy Research. Jan; 18(1): pp. 43-46 (2004).
Sano, Mitsuaki, et al. "Inhibitory Effects of Edible Higher Basidiomycetes Mushroom Extracts on Mouse Type IV Allergy". International Journal of Medicinal Mushrooms vol. 4, Issue 1: pp. 37-41 (2002).
Kim, Sun-Hyoung et al. "Anti-inflammatory and related pharmacological activities of the n-BuOH subfraction of mushroom *Phellinus linteus*". Journal of Ethnopharmacology. 93(1): pp. 141-146 (2004).
Padilha, Marina, M. et al. "Anti-inflammatory Activity of Aqueous and Alkaline Extracts from Mushrooms (*Agaricus plazei* Murill)". J Med Food. 12(2): pp. 359-364 (2009).
Smiderle, Fhernanada R. et al. "Immunopharmacolgy and Inflammation: Anti-inflammatory and analgesic properties in a rodent model of a (1->3),( 1->6)-linked (β-glucan isolated from Pleurotus pulmonarius". European Journal of Pharmacology vol. 597, Issues 1-3, pp. 86-91. (2008).
Lull, Cristina et al., "Antiinflammatory and Immunomodulating Properties of Fungal Metabolites" Mediators of Inflammation 2005(2): pp. 63-80 (2005).
Inoue, Atsuyuki et al., "Effect of Maitake (*Grifola frondosa*) D-Fraction on the Control of the T Lymph Node Th-1/Th-2 Proportion" Biol. Pharm. Bull. 25(4): pp. 536-540 (2002).

(Continued)

*Primary Examiner* — Rodney P Swartz
(74) *Attorney, Agent, or Firm* — Meunier Carlin & Curfman LLC

(57) ABSTRACT

A vitamin D2-enriched biomass of an edible fungus, extracts and compositions thereof are provided, for use in delaying onset of, treating, ameliorating or protecting from an immune-related or inflammatory related disease, disorder or condition, wherein the level of vitamin D2 in said biomass is at least 80 IU/gr.

18 Claims, 6 Drawing Sheets

(56) References Cited

OTHER PUBLICATIONS

Moradali, Mohammad-Fata et al., "Immunomodulating and anti-cancer agents in the realm of macromycetes fungi (macofungi)". International Immunopharmacology vol. 7, pp. 701-724 (2007).

Wasser, S.P., "Medicinal mushrooms as a source of antitumor and immunomodulating polysaccharides" Appl. Microbiol. Biotechnol. 60: pp. 258-274 (2002).

Kupfahl, C. et al., "Lentinan has a stimulatory effect on innate and adaptive immunity against murine Listeria monocytogenes infection". International Immunopharmacology 6: pp. 686-696 (2006).

Vetvicka, Vaclav et al., "Effects of marine β-1,3 glucan on immune reactions" International Immunopharmacology. vol. 4: pp. 721-730 (2004).

Akamatsu, Soichiro et al., "Hepatoprotective Effects of Extracts from Lentinus edodes Mycelia on Dimethylnitrosamine-Induced Liver Injury". Biol. Pharm. Bull. 27(12):pp. 1957-1960 (2004).

Watanabe, Aiko et al., "Protection against D-Galactosamine-Induced Acute Liver Injury by Oral Administration of Extracts from Lentinus edodes Mycelia". Biol. Pharm. Bull. 29(8): pp. 1651-1654. (2006).

Vetvicka, Vaclav et al., "Enhancing effects of new biological response modifier β-1,3 glucan sulfate PS3 on immune reactions" Biomedicine & Pharmacotherapy. 62: pp. 283-288 (2008).

Xystrakis, Emmanuel et. al., "Reversing the defective induction of IL-10- secreting regulatory T cells in glucocorticoid-resistant asthma patients". The Journal of Clinical Investigation. 116: pp. 146-155 (2006).

Smyk, Daniel S. et. al., "Vitamin D in autoimmune liver disease". Clin Res Hepatol Gastroenterol 37(5): pp. 535-545 (2013).

Agmon-Levin, Nancy et. al. "Vitamin D in Systemic and Organ-Specific Autoimmune Diseases". Clinic Rev Allerg Immunol 45: pp. 256-266 (2013).

Shapira, Yinon et. al., "Mycobacterium Tuberculosis, Autoimmunity, and Vitamin D". Clinic Rev Allerg Immunol 38: pp. 169-177 (2010).

Chen, Sheng et. al. "Modulatory Effects of 1,25-Dihydroxyvitamin D3 on Human B Cell Differentiation". J Immunol 179: pp. 1634-1647 (2007).

Kalaras, Michael D. et al., "Effects of Postharvest Pulsed UV Light Treatment of White Button Mushrooms (*Agaricus bisporus*) on Vitamin D2 Content and Quality Attributes" J. Agric. Food Chem. 60: pp. 220-225. (2012).

International Search Report dated May 23, 2016, from International Application No. PCT/IL2016/050053, 6 pages.

Written Opinion completed on May 15, 2016, from International Application No. PCT/IL2016/050053, 8 pages.

\* cited by examiner

Control

Vit D

LE

LE+Vit D

EXTRACTS OF EDIBLE FUNGI ENRICHED IN VITAMIN D AND COMPOSTIONS THEREOF AND THEIR USE IN THE TREATMENT OF IMMUNE-RELATED DISORDERS

FIELD OF THE INVENTION

The present invention relates in general to the use of edible fungi, enriched with vitamin D or supplemented therewith, for the treatment or prevention of immune-mediated disorders.

BACKGROUND OF THE INVENTION

Immune therapy involves the exposure of components of the immune system to various elements (cytokines, disease associated antigens and natural metabolites) to combat disease processes in which a non-regulated immune response is thought to play a role. Immune dysregulation is thought to play a major part in the pathogenesis or disease course of a great number of disease processes, including various neoplastic, inflammatory, infectious and genetic entities.

The Role of Fungi in the Modulation of the Immune System.

*Lentinula, Pleurotus, Auricularia, Flammulina, Tremella, Hericium,* and *Grifola* fungi have various degrees of immunomodulatory, lipid-lowering, antitumor beneficial or therapeutic effects without any significant toxicity.

Fungi have been valued by humans as an edible and medical resource. Fungi have long been known for their nutritious benefits. They are an excellent source of selenium, riboflavin, pantothenic acid copper, niacin, potassium and phosphorous. In particular selenium is needed for proper function of important antioxidants which work to reduce the levels of damaging free radicals in the body. Fractions from medical fungi were used as medicine in the Far East. Extracts and isolated metabolites from fungi can modulate immune responses [Lull, C. et al., Mediators Inflamm. 2005:63-80 (2005)]. This can result in an enhanced innate and acquired disease resistance. The major immunomodulating effects of these active substances derived from fungi include mitogenicity and activation of immune effector cells, such as lymphocytes, macrophages, and natural killer cells, resulting in the production of cytokines, including interleukins (ILs), tumor necrosis factor alpha (TNF-α, and interferon gamma (IFN-γ) [Lull et al. (2005), Ibid.]. The ability of selective fungal extracts to modulate the differentiation capacity of CD4(+) T cells to mature into Th1 and/or Th2 subsets has been shown recently.

Previous data suggested that these extracts may have profound effects in Th1 or Th2 immune-mediated disorders [Inoue, A. et al., Biol. Pharm. Bull. 25:536-540 (2002)]. A number of bioactive molecules, most of them polysaccharides, with antitumoral properties indicating induction of a Th1 response, have been identified in many mushroom-derived formulations [Moradali, M. F. et al., Int. Immunopharmacol. 7:701-724 (2007)].

The major immune modulating effects of these active substances include mitogenicity and activation of immune effector cells, such as lymphocytes, macrophages and Natural Killer T (NKT) cells.

Fungal derivates can affect different parts of the immune system, including macrophage activation by induction of TNF-α, IL-6 and IL-1, dendritic cell activation and various effects on T cells [Moradali et al. (2007), Ibid.]. *Lentinula edodes* was described as T-cell oriented adjuvant, skewing the Th1/Th2 balance to Th1 by distinctive induction of IL-12 from activated macrophages [Wasser S. P., Appl. Microbiol. Biotechnol. 60:258-274 (2002)].

The Role of Shiitake in Immuno-Modulation.

Lentinan, a (1-3)-beta glucan from *Lentinula edodes*, is licensed as an immunostimulatory drug [Kupfahl, C. et al., Int. Immunopharmacol. 6:686-696 (2006)]. Pre-treatment of mice with lentinan resulted in increased concentrations of TNF-α, IL-12 and IFN-γ and also an increased number of Listeria monocytogenes specific CD8 T cells in the spleen. The bacterial burden in spleen and liver of mice was significantly reduced during primary and secondary Listeria infection after lentinan pre-treatment of mice. *Lentinula edodes* (Shiitake) and its active component, the polysaccharide lentinan were found effective against various tumors. The mechanism of its action is not understood. Several studies showed its efficacy in various gastrointestinal tumors, gynecologic tumors, as well as leukemia and lymphoma. In most of these studies Shiitake augments the effect of other drugs.

It was suggested that mushrooms do not attack cancer cells directly, but produce their anti-tumor effects by activating different immune responses in the host [Yvin, J. C., Int. Immunopharmacol, 4:721-730 (2004)]. Shiitake was also shown to be a hepatoprotective and anti-fibrotic agent. In dimethylnitrosamine-induced hepatitis, Shiitake decreased the blood levels of aminotransferases by inhibiting the over accumulation of collagen fibrils and suppressed the over expression of genes for alpha-smooth muscle actin and heat-shock protein 47 [Akamatsu, S. et al., Biol. Pharm. Bull. 27:1957-1960 (2004)]. Shiitake also inhibited the morphologic change and proliferation of isolated rat hepatic stellate cells (HSCs), which play a central role in liver fibrosis, in a dose-dependent manner and without cytotoxicity [Akamatsu et al. (2004), Ibid.]. Interestingly the hepatoprotective effects of Shiitake were also observed after oral administration [Watanabe, A. et al., Biol. Pharm. Bull. 29:1651-1654 (2006)]. In a D-galactosamine (GalN)-induced liver injury model in rats oral administration of Shiitake caused less leakage of aminotransferases and improves the degree of histological injury [Watanabe et al. (2006), Ibid.]. As a result, several studies were conducted, in order to characterize the specific active component, and its immune modulating effect however, this effect was never tested in immune mediated disorders [Vetvicka, V. et al., Biomed. Pharmacother. 2008 June; 62(5) 283-8].

WO 2006/007848 showed that polypeptides and polysaccharides produced by the fungus and secreted to the extracellular environment of the liquid growth medium exhibit an immune modulatory effect towards a pro-inflammatory response which may be beneficial in the treatment of immune compromised patients.

The Role of the Liver in Immune System Processes.

The role of liver in the pathogenesis of different immune mediated disorders is well known. The liver contains a mixture of lymphocytes consisting of both conventional T and B cells, and a distinct population of resident liver lymphocytes. Furthermore the liver is a specific site for trapping and destruction of activated T cells. The exact role of the liver in immune cell trapping and destruction is not fully understood, one theory suggests that cells that are already starting apoptosis process are sequestrated in the liver. The second theory suggest that the liver has an active role in the immune process by destructing activated T cells due to a local tolerance mechanism that causes clonal deletion.

Vitamin D is a Known Immune Modulator.

Beyond its critical function in calcium homeostasis, vitamin D has recently been found to play an important role, in the modulation of the immune/inflammation system, via regulating the production of inflammatory cytokines and inhibiting the proliferation of proinflammatory cells, both of which are crucial for the pathogenesis of inflammatory diseases. Several studies have associated lower vitamin D status with increased risk and unfavorable outcome of acute infections. Vitamin D supplementation bolsters clinical responses to acute infection. Moreover, chronic inflammatory diseases, such as atherosclerosis-related cardiovascular disease, asthma, inflammatory bowel disease, chronic kidney disease, nonalcoholic fatty liver disease, and others, tend to have lower vitamin D status, which may play a pleiotropic role, in the pathogenesis of the diseases.

Vitamin D is associated with enhancement of anti-inflammatory IL-10 secretion by $CD4^+$ Treg cells in Steroid-resistant Asthma patients (Xystrakis et. al., Reversing the defective induction of IL-10-secreting regulatory T cells in glucocorticoid-resistant asthma patients. J. Clin. Invest. (2006) 116:146-155); Suppression of pro-inflammatory IL-2, TNF-α, and IFN-γ secretion by Th1 cells (Smyk et. al., Vitamin D in autoimmune liver disease. Clin Res Hepatol Gastroenterol (2013) 37(5):535-545); Induction of immune tolerance by promotion of tolerogenic dendritic cell function (Agmon-Levin et. al. Vitamin D in Systemic and Organ-Specific Autoimmune Diseases. Clinic Rev Allerg Immunol (2013) 45:256-266); Induction of macrophage response to TB infections (Shapora et. al., *Mycobacterium Tuberculosis*, Autoimmunity, and Vitamin D. Clinic Rev Allerg Immunol (2010) 38:169-177); and decreased proliferation and antibody production by B cells (Chen et. al. Modulatory Effects of 1,25-Dihydroxyvitamin D3 on Human B Cell Differentiation. J Immunol (2007) 179:1634-1647).

Mushrooms have relatively high levels of ergosterol, which, under the action of UV light gets converted to ergocalciferol (known as vitamin D2) [Kalaras et al., J. Agric. Food Chem. 2012. 60: 220-225; DE202010016402; U.S. Pat. No. 8,545,915; US20110091579; CA2759246]. Vitamin D2 is inactive, but on consumption is converted to 25-hydroxycholecalciferol in the liver, then to 1,25-dihydroxycholecalciferol (vitamin D3) by the kidneys.

There remains an unmet need for improved fungi or fungi-derived products that could be used for treatment of immune-related disorders.

SUMMARY OF INVENTION

In one aspect, the present invention provides a vitamin D2-enriched biomass of an edible fungus, for use in delaying onset of, treating, ameliorating or protecting from an immune-related or inflammatory related disease, disorder or condition, wherein the level of vitamin D2 in said biomass is at least 80 IU/gr (dry weight), or the vitamin D2 is present in said biomass at a level that is at least about two times higher than the level of vitamin D2 in an biomass of an edible fungus that has not been exposed to UVB radiation.

In another aspect, the present invention is directed to an extract obtained from the biomass defined herein.

In a further aspect, the present invention provides a composition comprising (a) a biomass or an extract as defined above; or (b) a biomass or extract of a native untreated edible fungus and vitamin D2, wherein the level of vitamin D2 in the composition comprising said biomass or extract of (b) is at least 80 IU/gr.

In an additional aspect, the present invention provides a pharmaceutical composition comprising a pharmaceutically acceptable carrier and a biomass, an extract or a composition as defined herein.

In yet an additional aspect, the present invention provides a method for delaying onset of, treating, ameliorating or protecting from an immune-related or inflammatory related disease, disorder or condition in a mammalian subject, said method comprising administering to said subject a therapeutically effective amount of the biomass, the extract, or the pharmaceutical composition as defined herein.

In still a further aspect, the present invention provides the biomass, the extract, or the pharmaceutical composition as defined herein for use in the manufacture of a medicament for delaying onset of, treating, ameliorating or protecting from an immune-related or inflammatory related disease, disorder or condition.

In still an additional aspect, the present invention is directed to a kit for use in delaying onset of, treating, ameliorating or protecting from an immune-related or inflammatory related disease, disorder or condition, said kit comprising: (a) a biomass of an edible fungus; (b) an extract obtained from an edible fungus; or (c) a composition comprising an extract obtained from an edible fungus; (d) vitamin D2; and (e) a leaflet with instructions for administration of a combination of (a), (b) or (c) and (d).

This effect was statistically significant (P<0.005) in the groups fed with Shiitake and GF but not in the group fed FV.

Figure 7:
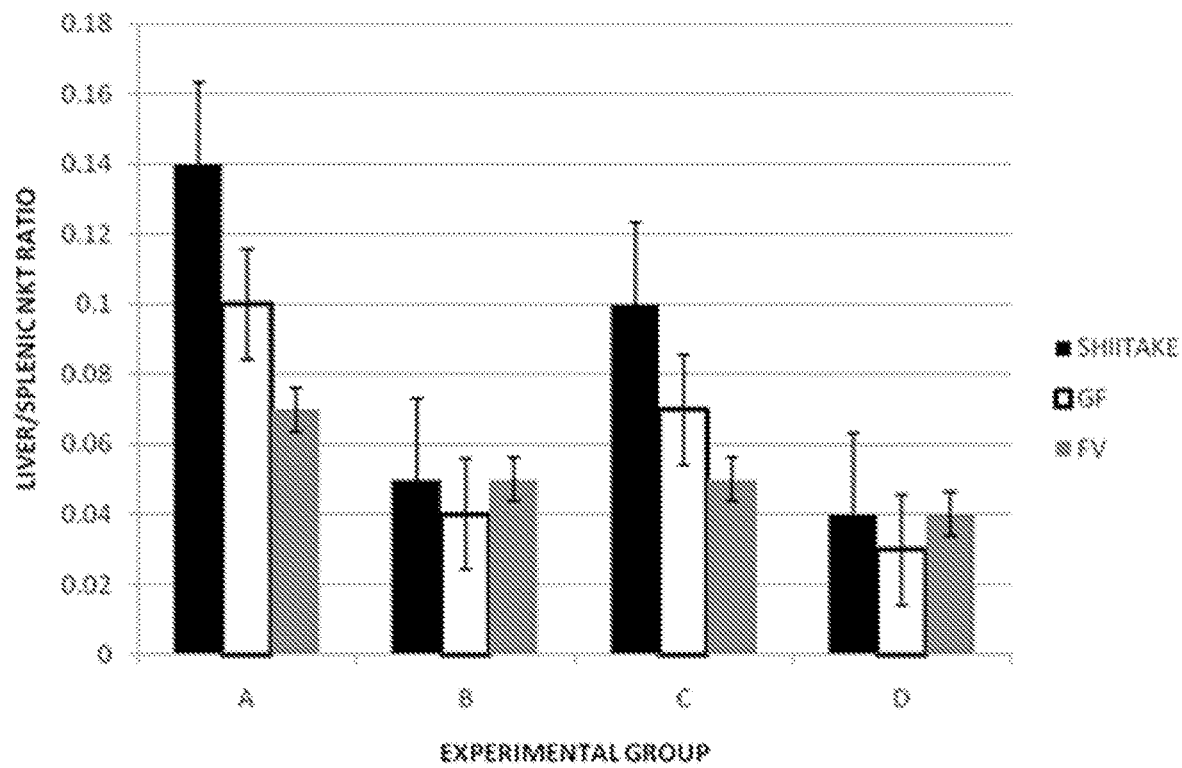

FIG. 7 shows the effect of the mushroom preparations on the liver/spleen NKT cell ratio. FACS analysis was performed on spleen- and liver-derived lymphocytes from mice with (Groups A and B) and without (Groups C and D) experimentally induced colitis. Mice in Groups A and C were fed mushroom preparations as indicated, and mice in Groups B and D were fed BSA. Liver NKT cells increased in Groups A and C compared with mice in Group B and in Group D (control). The spleen/liver NKT cell ratio was calculated.

Figure 8:
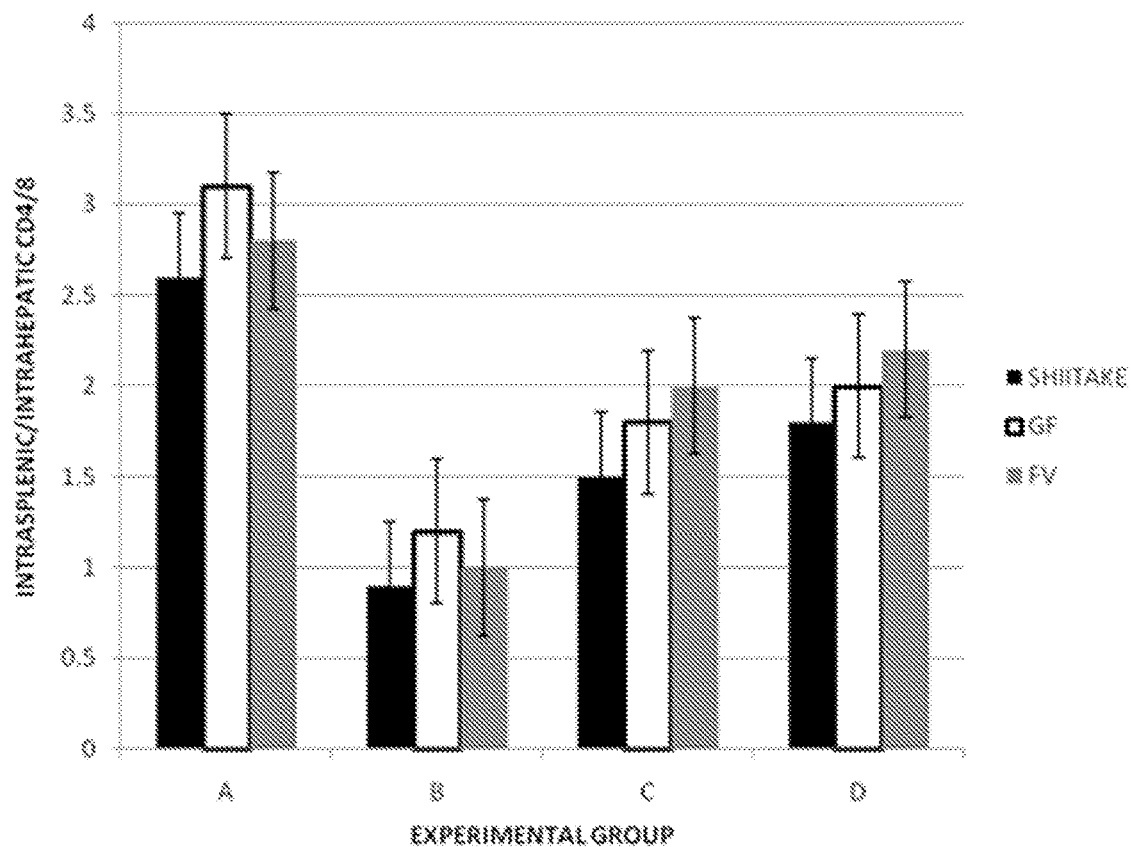

FIG. 8 shows the effect of the mushroom preparations on the splenic/liver CD4/CD8 ratio. FACS analysis was performed on spleen- and liver-derived lymphocytes from mice with (Groups A and B) and without (Groups C and D) experimentally induced colitis. Mice in Groups A and C were fed mushroom preparations as indicated, and mice in Groups B and D were fed BSA. The effect of mushroom preparations administration on the splenic/hepatic CD4/CD8 ratio is shown. The peripheral(spleen)/intrahepatic(liver) ratio of CD4/CD8 ratio was similar in group C and D. Mushroom administration in mice with colitis (Group A) induce a significant increase in splenic/liver CD4/CD8 ratio comparative to colitis-only group (B) mice. This effect was statistically significant (P<0.005) for all the three mushroom preparations studied.

Figure 9:
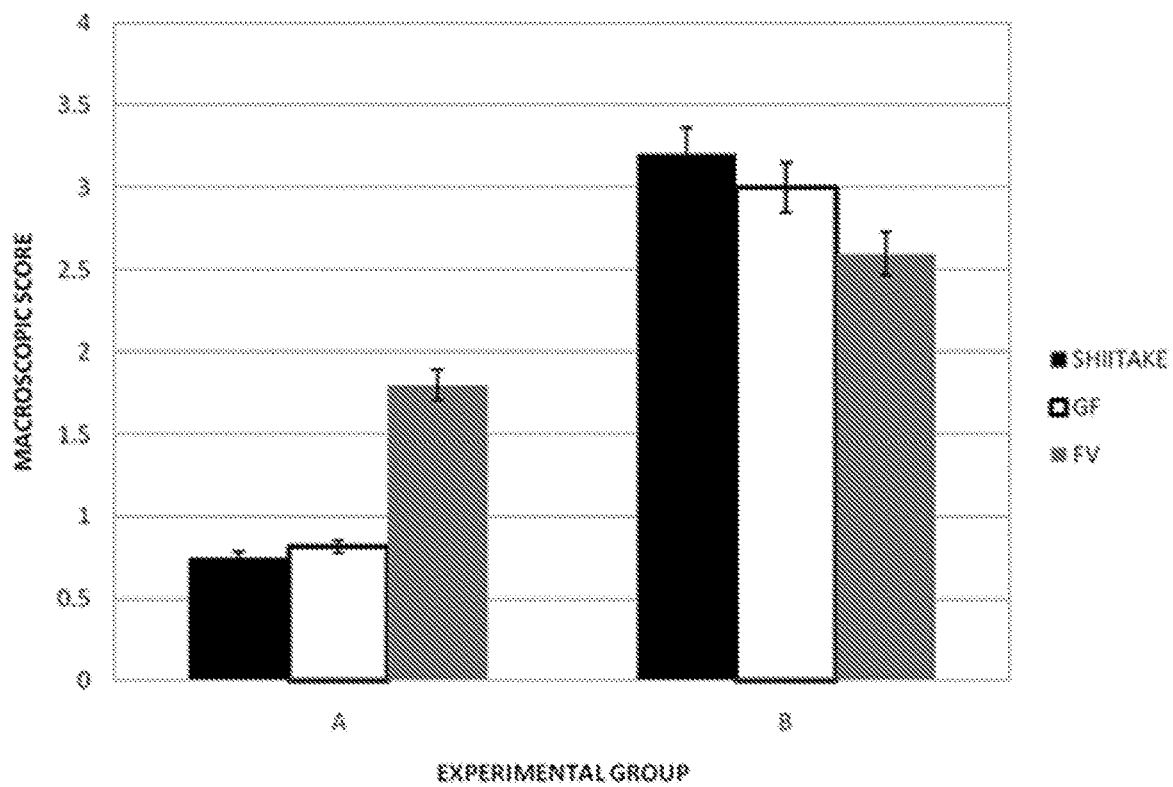

FIG. 9 the effect of the mushroom preparations on the macroscopic scores of inflammation in mice with experimentally induced colitis (Groups A and B). Mice in Group A were given mushroom preparations, and mice in Group B were given BSA as a control. Mushroom administration significantly (P<0.005) alleviated the severity of colitis in Group A compared with Group B.

Figure 10:
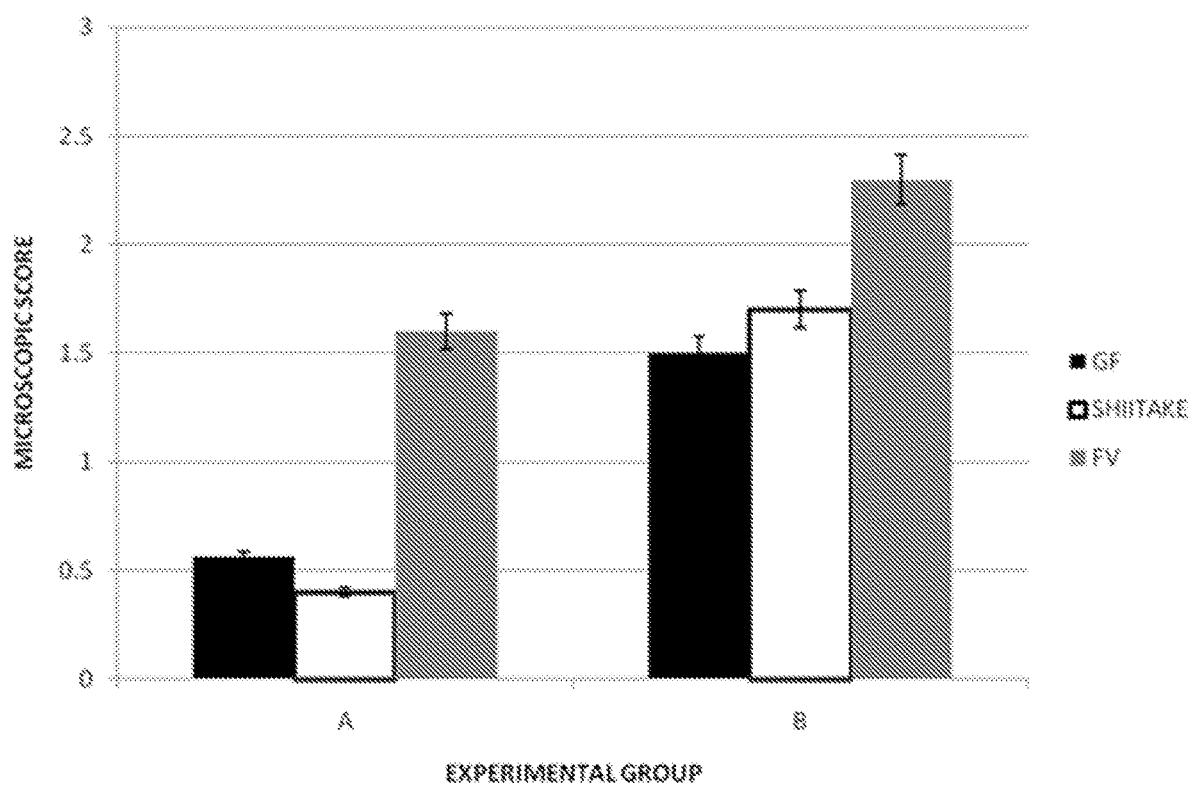

FIG. 10 shows the effect of the mushroom preparations on the microscopic scores of inflammation in mice with experimentally induced colitis (Groups A and B). Mice in Group A were given mushroom preparations, and mice in Group B were given BSA as a control. Mushroom administration alleviated the severity of colitis in Group A mice compared with mice in Group B.

DETAILED DESCRIPTION OF THE INVENTION

The present invention is based on the finding that biomass derived from mushrooms enriched with vitamin D2 exert a synergistic effect on the immune system. Freeze-dried formulations prepared from *Lentinula edodes* (Shiitake) enriched with vitamin D2 demonstrate a synergistic effect on immune-related liver disease in mice as evidenced by reduced alanine aminotransferase (ALT) serum levels and reduced incidence of severe liver injury in these mice (when compared with vitamin D2 or formulations prepared from *Lentinula edodes* (Shiitake) having normal levels of vitamin D2).

In view of the above, the present invention provides, in one aspect, a vitamin D2-enriched biomass of an edible fungus, for use in preventing, delaying onset of, treating, ameliorating or protecting from an immune-related or inflammatory related disease, disorder or condition, wherein the level of vitamin D2 in said biomass is at least 80 IU/gr freeze-dried biomass (i.e. on dry weight basis), or the vitamin D2 is present in said biomass at a level that is at least about two times higher than the level of vitamin D2 in a biomass of an edible fungus that has not been exposed to UVB radiation (on dry weight basis).

The term "biomass" as used herein refers to organic matter derived from the fungus by for example harvesting, separating distinct parts from each other, mincing, cutting, shredding, and/or drying/freeze-drying the biomass, but not including for example extracting certain fractions from the biomass using solvents.

It was found in accordance with the present invention that *Lentinula edodes* contains on average 64 IU/gr and 126 IU/gr of vitamin D2 before and after UVB-treatment, respectively and that *Pleurotus ostreatus* contains on average 49 IU/gr and 148 IU/gr of vitamin D2 before and after UVB-treatment, respectively. In mushrooms grown in the dark, the level of vitamin D2 is undetectable (see Example 4 and Kalaras, 2012). It was further found by the inventors that oral administration to mice of 1.125 IU of vitamin D2 in 7.5 mg freeze-dried mushroom (150 IU/gr) twice or three times daily during three consecutive days prior to induction of immune-related liver disease was highly efficacious as described above and in the Examples.

Thus, in certain embodiments, the level of vitamin D2 in the biomass is in the range of about 80-5000 IU/gr freeze-dried biomass (on dry weight basis), for example about 80-3000 IU/gr. Thus, the level of vitamin D2 may be 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, 1500, 1510, 1520, 1530, 1540, 1550, 1560, 1570, 1580, 1590, 1600, 1610, 1620, 1630, 1640, 1650, 1660, 1670, 1680, 1690, 1700, 1710, 1720, 1730, 1740, 1750, 1760, 1770, 1780, 1790, 1800, 1810, 1820, 1830, 1840, 1850, 1860, 1870, 1880, 1890, 1900, 1910, 1920, 1930, 1940, 1950, 1960, 1970, 1980, 1990, 2000, 2010, 2020, 2030, 2040, 2050, 2060, 2070, 2080, 2090, 2100, 2110, 2120, 2130, 2140, 2150, 2160, 2170, 2180, 2190, 2200, 2210, 2220, 2230, 2240, 2250, 2260, 2270, 2280, 2290, 2300, 2310, 2320, 2330, 2340, 2350, 2360, 2370, 2380, 2390, 2400, 2410, 2420, 2430, 2440, 2450, 2460, 2470, 2480, 2490, 2500, 2510, 2520, 2530, 2540, 2550, 2560, 2570, 2580, 2590, 2600, 2610, 2620, 2630, 2640, 2650, 2660, 2670, 2680, 2690, 2700, 2710, 2720, 2730, 2740, 2750, 2760, 2770, 2780, 2790, 2800, 2810, 2820, 2830, 2840, 2850, 2860, 2870, 2880, 2890, 2900, 2910, 2920, 2930, 2940, 2950, 2960, 2970, 2980, 2990, 3000, 3010, 3020, 3030, 3040, 3050, 3060, 3070, 3080, 3090, 3100, 3110, 3120, 3130, 3140, 3150, 3160, 3170, 3180, 3190, 3200, 3210, 3220, 3230, 3240, 3250, 3260, 3270, 3280, 3290, 3300, 3310, 3320, 3330, 3340, 3350, 3360, 3370, 3380, 3390, 3400, 3410, 3420, 3430, 3440, 3450, 3460, 3470, 3480, 3490, 3500, 3510, 3520, 3530, 3540, 3550, 3560, 3570, 3580, 3590, 3600, 3610, 3620, 3630, 3640, 3650, 3660, 3670, 3680, 3690, 3700, 3710, 3720, 3730, 3740, 3750, 3760, 3770, 3780, 3790, 3800, 3810, 3820, 3830, 3840, 3850, 3860, 3870, 3880, 3890, 3900, 3910, 3920, 3930, 3940, 3950, 3960, 3970, 3980, 3990, 4000, 4010, 4020, 4030, 4040, 4050, 4060, 4070, 4080, 4090, 4100, 4110, 4120, 4130, 4140, 4150, 4160, 4170, 4180, 4190, 4200, 4210, 4220, 4230, 4240, 4250, 4260, 4270, 4280, 4290, 4300, 4310, 4320, 4330, 4340, 4350, 4360, 4370, 4380, 4390, 4400, 4410, 4420, 4430, 4440, 4450, 4460, 4470, 4480, 4490, 4500, 4510, 4520, 4530, 4540, 4550, 4560, 4570, 4580, 4590, 4600, 4610, 4620, 4630, 4640, 4650, 4660, 4670, 4680, 4690, 4700, 4710, 4720, 4730, 4740, 4750, 4760, 4770, 4780, 4790, 4800, 4810, 4820, 4830, 4840, 4850, 4860, 4870, 4880, 4890, 4900, 4910, 4920, 4930, 4940, 4950, 4960, 4970, 4980, 4990 or 5000 IU/gr freeze-dried biomass (on dry weight basis). It is well-known in the field of vitamins that 1 µg vitamin D2 equals 40 IU.

In certain embodiments, the vitamin D2 is present in said biomass at a level that is at least about two to 100 times, or 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 times, higher than the level of vitamin D2 in a biomass of an edible fungus that has not been exposed to UVB radiation (on dry weight basis). Since in mushrooms that have grown in the dark, the level of vitamin D2 is undetectable (see Example 4 and Kalaras, 2012), for purpose of comparison, the level is assumed to be 1 IU/gr and not 0 IU/gr.

In certain embodiments, the biomass is obtained from a UVB-treated edible fungus. The method of exposing fungi to short pulses of UVB light to cause an increase in vitamin D2 levels is well known in the art as described for example in the Examples below.

The terms "UVB" or "UVB-light", a.k.a "medium wave ultraviolet radiation", are used interchangeably herein and refer to electromagnetic radiation having a wave-length range of about 280-315 nm.

The fungus used by the method of the invention may be any edible fungus, such as a fungus forming a fungal mycelium and fruiting bodies.

In certain embodiments, the biomass is obtained from the fruiting body or mycelium of the edible fungus.

In certain embodiments, the biomass is obtained from edible fungus belonging to the Basidiomycota Division, such as a fungus selected from the group consisting of *Lentinula edodes, Flammulina velutipes, Grifola ulmarium, Grifola frondosa, Pleurotus ostreatus, Pleurotus brasilensis, Pholiota nameko, Tricholoma matsutake, Lyophyllum shimeji, Lyophyllum ulmarium, Coriolus versicolor, Schizophyllum commune, Crepidotus variabilis, Auricularia aurcula-judae, Fomes fomentarius, Volvavella volvacea, Ganoderma lucidum, Ganoderma applanatum, Fomitopsis pinicola, Dictyophora indusiata, Sparassis crispa, Agaricus blazei, Peziza vesiculosa, Tremella fuciformis,* and *Hericuim erinaceus.*

In certain embodiments, the edible fungus is selected from *Lentinula edodes, Flammulina veluptipes, Pleurotus ostreatus* and *Grifolda frondosa.*

In another aspect, the present invention is directed to an extract obtained from the biomass defined herein. The term "extract" as herein refers to a substance made by extracting a part of a raw material, such as the biomass of a fungus, by using a solvent.

The extract may be solvent-free, because the solvent has been removed from the extract for example by evaporation, or it may be obtained with a solvent selected from the group consisting of water; saline; steam; an alcohol, such as methanol, ethanol, propanol and butanol; an organic solvent, such as ethyl acetate, chloroform, acetonitrile, hexane, cyclohexane, isooctane and dichloromethane; carbon dioxide or combinations thereof.

The extract may comprise equivalent or higher levels of vitamin D2 to those described above for the biomass. For example, an extract obtained from a certain amount of vitamin D2-enriched biomass of an edible fungus would comprise an amount of vitamin D2 that is at least two to 100 times, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 times, higher than the amount of vitamin D2 in an extract obtained from an equal amount of an edible fungus that has not been exposed to UVB radiation (measured in e.g. IU and on dry weight basis).

It has further been found in accordance with the present invention that a *Lentinula edodes* (Shiitake) powdered preparation of fruiting bodies, a polysaccharide extract from *Grifola frondosa* (GF) and a protein extract from *Flammulina velutipes* (FV) exhibit beneficial effect on animal model of 2,4,6-trinitrobenzene sulphonic acid (TNBS) colitis. Administration of this formulation significantly alleviated the macroscopic and microscopic score of colitis. The beneficial effect of these fungi preparations was associated with an altered Natural Killer T (NKT) lymphocyte distribution and as demonstrated for Shiitake, this effect was also associated with a marked reduction in the number of disease target antigen-IFNγ producing colonies. These results indicate an immune modulatory towards an anti-inflammatory response.

The inventors were able to show that the systemic effect of different preparations of the three fungi, *Lentinula edodes* (Shiitake), *Grifola frondosa* (GF) and *Flammulina velutipes* (FV), was associated with CD8 T cells trapping in the liver indicative of the role played by the liver in mediating the systemic induction of tolerance.

Thus, in certain embodiments, the present invention provides an extract obtained from a biomass of an edible fungus, said extract comprising water soluble polysaccharides or proteins, for use in preventing, delaying onset of, treating, ameliorating or protecting from an immune-related or inflammatory related disease, disorder or condition. The edible fungus may be untreated or pretreated with UV as disclosed herein. It may belong to the Basidiomycota Division, such as those described herein above, and is for example *Flammulina veluptipes* or *Grifolda frondosa.*

In certain embodiments, the soluble polysaccharides are extracted with a solvent comprising essentially of water. The proteins may be extracted with a solvent comprising saline.

In a further aspect, the present invention provides a composition comprising (a) a biomass or an extract as defined above; or (b) a biomass or extract of a untreated edible fungus and vitamin D2, wherein the level of vitamin D2 in the composition comprising said biomass or extract of (b) is at least 80 IU/gr, or the composition of (b) has a concentration of vitamin D2 that is about two to 100 times, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 times, higher than the level of vitamin D2 in a composition having the same amount of biomass or extract of an edible fungus that has not been exposed to UVB radiation. The extract of (b) may be an extract obtained by extraction with water and may be enriched in polysaccharides (relative to the biomass of the same mushroom); or it may be obtained by extraction with saline and may thus be enriched with proteins (relative to the biomass of the same mushroom).

In certain embodiments, at least some of the vitamin D2 of (b) originates from a source different from the biomass or extract of the edible fungus of (b), i.e. the vitamin D2 has been added to the biomass or extract of the untreated edible fungus and originates, for example, from UV irradiated yeast.

In an additional aspect, the present invention provides a pharmaceutical composition comprising a pharmaceutically acceptable carrier and a biomass, an extract or a composition as defined herein.

Pharmaceutical compositions for use in accordance with the present invention may be formulated in conventional manner using one or more physiologically acceptable carriers or excipients, for example according to Remington's Pharmaceutical Sciences, Gennaro A. R. ed., Mack Publishing Co., Easton, Pa., 1990, and especially pp. 1521-1712 therein, fully incorporated herein by reference.

The carrier(s) must be "acceptable" in the sense of being compatible with the other ingredients of the composition and not deleterious to the recipient thereof. The following exemplification of carriers, modes of administration, dosage forms, etc., are listed as known possibilities from which the carriers, modes of administration, dosage forms, etc., may be selected for use with the present invention. Those of ordinary skill in the art will understand, however, that any given formulation and mode of administration selected should first be tested to determine that it achieves the desired results.

The term "carrier" refers to a diluent, adjuvant, excipient, or vehicle with which the active agent is administered. The carriers in the pharmaceutical composition may comprise a binder, such as microcrystalline cellulose, polyvinylpyrrolidone (polyvidone or povidone), gum tragacanth, gelatin, starch, lactose or lactose monohydrate; a disintegrating agent, such as alginic acid, maize starch and the like; a lubricant or surfactant, such as magnesium stearate, or sodium lauryl sulphate; and a glidant, such as colloidal silicon dioxide.

Methods of administration include, but are not limited to, parenteral, e.g., intravenous, intraperitoneal, intramuscular, subcutaneous, mucosal (e.g., oral, intranasal, buccal, vaginal, rectal, intraocular), intrathecal, topical and intradermal routes. Administration can be systemic or local. In certain embodiments, the pharmaceutical composition is adapted for oral administration.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the active compound.

For buccal administration, the compositions may take the form of tablets or lozenges formulated in conventional manner.

The compositions may be formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use.

The compositions may also be formulated in rectal compositions such as suppositories or retention enemas, e.g., containing conventional suppository bases such as cocoa butter or other glycerides.

For administration by inhalation, the compositions for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator may be formulated containing a powder mix of the compound and a suitable powder base such as lactose or starch.

In particular, the biomass, extract or pharmaceutical composition of mushrooms enriched with vitamin D2, may be administered in a form selected from the group consisting of orally-active powders, pills, capsules, teas, extracts, dried extracts, sublinguals, sprays, dispersions, solutions, suspensions, emulsions, foams, syrups, lotions, ointments, gels, pastes, dermal patches, injectables, vaginal creams and suppositories.

It should be appreciated that the fungal derivatives of the invention, i.e. the biomass, extract or pharmaceutical composition of the present invention, may be used in the manufacture of or formulated as health foods, functional foods, nutrition supplement, health drinks, and functional drinks suitable for human beings. Said food and drink can be prepared by combining fungal derivatives and additives necessary for health foods or functional foods, with a liquid vehicle (such as water, milk, vegetable oil, juice and the like) or with ingestible solid or semi-solid foodstuff. Flavorings and sweeteners usable in food and drink can be used to form a solution usable in the form of drink, tablets, granules, capsules, jelly or ice cream. The food and drink can be used for prevention not only in healthy persons but also for delaying onset of, treating, ameliorating or protecting from an immune-related or inflammatory related disease, disorder or condition. For animals other than human, the food and drink can be applied in feed, pharmaceutical products, and pharmaceutical compositions.

The determination of the doses of the active ingredient to be used for human use is based on commonly used practices in the art, and will be finally determined by physicians in clinical trials. An expected approximate equivalent dose for administration to a human can be calculated based on the in vivo experimental evidence disclosed herein below, using known formulas (e.g. Reagan-Show et al. (2007) Dose translation from animal to human studies revisited. The FASEB Journal 22:659-661). According to this paradigm, the adult human equivalent dose (mg/kg body weight) equals a dose given to a mouse (mg/kg body weight) multiplied with 0.081.

For example, the daily amount administered to the subject of treatment according to the present invention may be between about 0.05 mg to 500 mg, 0.5 mg to 100 mg, about 1 mg to 10 mg, or about 2.5 mg of powdered biomass preparation of fresh, dried or freeze dried fruiting bodies or mycelium of the edible fungus per kg of body weight of the subject. This amount may be administered as biomass, extract or in a pharmaceutical composition as defined herein. The edible fungus may belong to the Basidiomycota Division, such as those described herein above, and is for example *Lentinula edodes, Pleurotus ostreatus, Flammulina veluptipes* or *Grifolda frondosa*.

According to another example, the daily amount administered to the subject of treatment according to the present invention may be between about 0.05 mg to 500 mg, 0.5 mg to 100 mg, about 1 mg to 10 mg, or about 2.5 mg of protein extract as defined herein of fresh, dried or freeze dried mycelium or fruiting body of an edible fungus per kg body weight of the subject. This amount may be administered as extract or in a pharmaceutical composition as defined herein. The edible fungus may belong to the Basidiomycota Division, such as those described herein above, and is for example *Flammulina veluptipes*.

According to yet another example, the daily amount administered to the subject of treatment according to the present invention may be between about 0.05 mg to 500 mg, 0.5 mg to 100 mg, about 1 mg to 10 mg, or about 2.5 mg of polysaccharide extract as defined herein of fresh, dried or freeze dried mycelium or fruiting body of an edible fungus. This amount may be administered as extract or in a pharmaceutical composition as defined herein. The edible fungus may belong to the Basidiomycota Division, such as those described herein above, and is for example *Grifolda frondosa*.

As indicated above, generally, the dosage of fungal derivative needed to achieve a therapeutic effect will depend not only on such factors as the age, weight and sex of the patient and mode of administration, but also on the degree of disease progression and the potency of the particular derivative being utilized for the particular disorder of disease concerned.

In certain embodiments, the biomass, extract, composition or pharmaceutical composition of the present invention as defined herein is in the form of freeze-dried powder.

In certain embodiments, the biomass, extract, or the pharmaceutical composition of the present invention as defined herein is formulated for oral administration.

In certain embodiments, the immune-related or inflammatory related disease, disorder or condition related to by the present invention is selected from an autoimmune disease, a graft rejection pathology, an inflammatory disease, a nonalcoholic fatty liver disease, hyperlipidemia, atherosclerosis, metabolic syndrome and acute or chronic liver disease.

Autoimmune disease may include for example, Inflammatory Bowel Disease, Rheumatoid Arthritis, Diabetes, Asthma, acute and chronic Graft Versus Host Disease, Systemic Lupus Erythmatosus, Scleroderma, Multiple Sclerosis, Non Alcoholic Fatty Liver disease, Hyperlipidmia, Atherosclerosis, any part of the metabolic syndrome, overweight, SLE, Sjögren's syndrome, Polymyositis, Hashimoto's Thyroiditis, Ord's Thyroiditis, Addison's Disease, Antiphospholipid antibody syndrome (APS), Aplastic Anemia, Autoimmune Oophoritis, Acute Disseminated Encephalomyelitis (ADEM), Gestational Pemphigoid, Pemphigus Vulgaris, Goodpasture's syndrome, Idiopathic Thrombocytopenic Purpura, Kawasaki's Disease, Opsoclonus Myoclonus syndrome (OMS), Autoimmune Hemolytic Anemias, Pernicious Anemia, Polyarthritis (in dogs), Primary Biliary Cirrhosis, Reiter's syndrome, Takayasu's Arteritis, Wegener's Granulomatosis, Rheumatic Fever, Psoriasis, Grave's Disease, Myasthenia Gravis, Glomerulonephritis, and Autoimmune Hepatitis.

In certain embodiments, the immune-related or inflammatory related disease, disorder or condition is selected from inflammatory bowel disease, rheumatoid arthritis, type I diabetes, asthma, acute and chronic graft versus host disease, systemic lupus erythmatosus, scleroderma, multiple sclerosis, and immune mediated hepatitis, and in particular it is inflammatory bowel disease, e.g. ulcerative colitis or Crohn's disease.

In certain embodiments, the immune-related or inflammatory related disease, disorder or condition is selected from dyslipoproteinemia, obesity, non-insulin dependent diabetes mellitus (NIDDM), impaired glucose tolerance (IGT), blood coagulability, blood fibrinolysis defects and hypertension and nonalcoholic steatohepatitis (NASH) and fatty liver disease (NAFLD).

"Metabolic syndrome", or Syndrome X, is a combination of medical disorders that increase one's risk for cardiovascular disease and diabetes. Metabolic syndrome may therefore include at least two of the above mentioned immune-related disorders, i.e. at least two of dyslipoproteinemia, obesity, non-insulin dependent diabetes mellitus (NIDDM), impaired glucose tolerance (IGT), blood coagulability, blood fibrinolysis defects and hypertension and nonalcoholic steatohepatitis (NASH) and fatty liver disease (NAFLD).

Metabolic syndrome is a complex multi-factorial condition accompanied by an assortment of abnormalities including hypertension, hypertriglyceridemia, hyperglycemia, low levels of HDL-C, and abdominal obesity. Individuals with these characteristics typically manifest a prothrombotic and pro-inflammatory state. Available data suggest that metabolic syndrome is truly a syndrome (a grouping of risk factors).

According to the World Health Organization (WHO) Guideline, metabolic syndrome is present if an individual manifests: a) hypertension (>140 mm Hg systolic or >90 mm Hg diastolic); (b) dyslipidemia, defined as elevated plasma triglycerides (150 mg/dL), and/or low high-density lipoprotein (HDL) cholesterol (<35 mg/dL in men, <39 mg/dL in women); 3) visceral obesity, defined as a high body mass index (BMI) (30 kg/m2) and/or a high waist-to-hip ratio (>0.90 in men, >0.85 in women); and 4) microalbuminuria (urinary albumin excretion rate of 20 g/min). See WHO-International Society of Hypertension Guidelines for the Management of Hypertension. Guidelines Subcommittee. J. Hypertens. 17:151-183, 1999.

According to the National Cholesterol Education Program (NCEP ATP III study) metabolic syndrome is diagnosed if three (3) or more of the following five (5) risk factors are present: (1) a waist circumference >102 cm (40 in) for men or >88 cm (37 in) for women; (2) a triglyceride level of 150 mg/dL; (3) an HDL cholesterol level <40 mg/dL for men or <50 mg/dL for women; (4) blood pressure >130/85 mm Hg; or (5) a fasting glucose >110 mg/dL. JAMA 285: 2486-2497, 2001.

Each of the disorders associated with metabolic syndrome are risk factors in their own right, and can promote atherosclerosis, cardiovascular disease, stroke, and other adverse health consequences. However, when present together, these factors are predictive of increased risk of cardiovascular disease and stroke.

By "control" or "treat" it is meant that the symptoms of the metabolic syndrome shown in an individual are reduced in severity and/or in number. Such symptoms may include elevated blood glucose, glucose intolerance, insulin resistance, elevated triglycerides, elevated LDL-cholesterol, low high-density lipoprotein (HDL) cholesterol, elevated blood pressure, abdominal obesity, pro-inflammatory states, and pro-thrombotic states. By "prevent" or "control" or "treat" it is additionally or alternatively meant that the risk of developing associated diseases is reduced and/or the onset of such diseases is delayed. Such associated diseases include cardiovascular disease, coronary heart disease and other diseases related to plaquing of the artery walls and diabetic conditions.

All types of obesity may be controlled or treated in accordance with the invention, including endogenous obesity, exogenous obesity, hyperinsulinar obesity, hyperplastic-hypertrophic obesity, hypertrophic obesity, hypothyroid obesity and morbid obesity. However, inflammation-mediated obesity may be treated particularly effectively in accordance with the invention. By "prevent" or "control" or "treat" it is meant that body weight gain, specifically body fat gain, is slowed down, stopped or reversed, resulting in a maintenance or decrease in body weight. A decrease in weight or body fat may protect against cardiovascular disease by lowering blood pressure, total cholesterol, LDL cholesterol and triglycerides, and may alleviate symptoms associated with chronic conditions such as hypertension, coronary heart disease, type 2 diabetes, osteoarthritis, sleep apnea and degenerative joint disease.

Diabetic conditions include, for example, type 1 diabetes, type 2 diabetes, gestational diabetes, pre-diabetes, slow onset autoimmune diabetes type 1 (LADA), hyperglycemia, and metabolic syndrome. For the purposes of treatment, the diabetes may be overt, diagnosed diabetes, e.g., type 2 diabetes, or a pre-diabetic condition.

Diabetes mellitus (generally referred to herein as "diabetes") is a disease that is characterized by impaired glucose regulation. Diabetes is a chronic disease that occurs when the pancreas fails to produce enough insulin or when the body cannot effectively use the insulin that is produced, resulting in an increased concentration of glucose in the blood (hyperglycemia). Diabetes may be classified as type 1 diabetes (insulin-dependent, juvenile, or childhood-onset diabetes), type 2 diabetes (non-insulin-dependent or adult-onset diabetes), LADA diabetes (late autoimmune diabetes of adulthood) or gestational diabetes. Additionally, intermediate conditions such as impaired glucose tolerance and impaired fasting glycemia are recognized as conditions that indicate a high risk of progressing to type 2 diabetes.

In type 1 diabetes, insulin production is absent due to autoimmune destruction of pancreatic beta-cells. There are several markers of this autoimmune destruction, detectable in body fluids and tissues, including islet cell autoantibodies, insulin autoantibodies, glutamic acid decarboxylase autoantibodies, and tyrosine phosphatase ICA512/IA-2 autoantibodies. In type 2 diabetes, comprising 90% of diabetics worldwide, insulin secretion may be inadequate, but peripheral insulin resistance is believed to be the primary defect. Type 2 diabetes is commonly, although not always, associated with obesity, a cause of insulin resistance Type 2 diabetes is often preceded by pre-diabetes, in which blood glucose levels are higher than normal but not yet high enough to be diagnosed as diabetes. The term "pre-diabetes," as used herein, is interchangeable with the terms "Impaired Glucose Tolerance" or "Impaired Fasting Glucose," which are terms that refer to tests used to measure blood glucose levels.

Chronic hyperglycemia in diabetes is associated with multiple, primarily vascular complications affecting microvasculature and/or macrovasculature. These long-term complications include retinopathy (leading to focal blurring, retinal detachment, and partial or total loss of vision), nephropathy (leading to renal failure), neuropathy (leading to pain, numbness, and loss of sensation in limbs, and potentially resulting in foot ulceration and/or amputation), cardiomyopathy (leading to heart failure), and increased risk of infection. Type 2, or noninsulin-dependent diabetes mellitus (NIDDM), is associated with resistance of glucose-utilizing tissues like adipose tissue, muscle, and liver, to the physiological actions of insulin. Chronically elevated blood glucose associated with NIDDM can lead to debilitating complications including nephropathy, often necessitating dialysis or renal transplant; peripheral neuropathy; retinopathy leading to blindness; ulceration and necrosis of the lower limbs, leading to amputation; fatty liver disease, which may progress to cirrhosis; and susceptibility to coronary artery disease and myocardial infarction. By "prevent" it is meant that the risk of developing of diabetes is reduced or the onset of the disease is delayed. By "control" or "treat" it is meant that the risk of developing associated complications is reduced and/or the onset of such complications is delayed.

A subject who has been classified as having a diabetic condition, and who is subject to treatment with mushrooms enriched with vitamin D, or their extracts, according to the methods of the present invention, may be monitored for efficacy of treatment by measuring any of the biomarkers and/or blood glucose indicators described herein, including but not limited to, glycosylated hemoglobin levels, C-peptide levels, fasting plasma glucose levels, and oral glucose tolerance test (OGTT) levels. For the biomarkers and/or blood glucose indicators described herein, efficacy of treatment can determined by quantitating the level of a biomarker or blood glucose indicator in a sample from a subject and determining whether the level of the biomarker or blood glucose indicator has reached or is approaching a threshold level. In some embodiments, a threshold level may correspond to a level of biomarker or blood glucose indicator that is a "normal" (i.e., non-diabetic) value according to standards known in the art, or a threshold level may correspond to a level of biomarker or blood glucose indicator that is a pre-diabetic or diabetic value according to standards known in the art.

In some embodiments, efficacy of treatment is determined by taking a first measurement of one or more of the biomarkers and/or blood glucose indicators in a subject prior to the start of treatment, and comparing the first measurement with secondary measurements of the same biomarker and/or blood glucose indicator in the subject at one or more time points after the onset of treatment, wherein a second measurement that has reached or exceeded a threshold value (either above or below, depending on the biomarker being measured), or is closer to the threshold value than the first measurement is to the threshold value, indicates that the treatment is efficacious.

Alternatively or additionally, efficacy of treatment may be monitored by determining whether there has been an amelioration of the secondary conditions and symptoms that are associated with the diabetic condition. For example, a subject being treated by the methods of the present invention can be monitored for improvement or reduction in symptoms of retinopathy (e.g., improvement in vision), nephropathy (e.g., improvement in kidney structure or function), neuropathy (e.g., improvement in nerve function), and/or cardiovascular disease (e.g., decreased blood pressure or lower lipid levels).

According to some embodiments of some aspects of the present invention, the biomass, extract or pharmaceutical compositions of the present invention enriched with vitamin D2 mushrooms can be used to delay onset of, protect from, prevent, treat and control liver diseases and disorders including hepatitis, cirrhosis, non-alcoholic steatohepatitis (NASH) (also known as non-alcoholic fatty liver disease-NAFLD), hepatotoxicity and chronic liver disease. In general, the terms 'delay onset of' `p prevent t`, `c control l` and `t treat t` encompass the prevention of the development of a disease or a symptom from a patient who may have a predisposition of the disease or the symptom but has yet been diagnosed to have the disease or the symptom; the inhibition of the symptoms of a disease, namely, inhibition or retardation of the progression thereof; and the alleviation of the symptoms of a disease, namely, regression of the disease or the symptoms, or inversion of the progression of the symptoms.

The term "liver disease" applies to many diseases and disorders that cause the liver to function improperly or to cease functioning, and this loss of liver function is indicative of liver disease. Thus, liver function tests are frequently used to diagnose liver disease. Examples of such tests include, but are not limited to, the following;

(1) Assays to determine the levels of serum enzymes such as lactate dehydrogenase (LDH), alkaline phosphatase (ALP), aspartate aminotransferase (AST), and alanine aminotransferase (ALT), where an increase in enzyme levels indicates liver disease. One of skill in the art will reasonably understand that these enzyme assays indicate only that the liver has been damaged. They do not assess the liver's ability to function. Other tests can be used to assay a liver's ability to function;

(2) Assays to determine serum bilirubin levels. Serum bilirubin levels are reported as total bilirubin and direct bilirubin. Normal values of total serum bilirubin are 0.1-1.0 mg/dl (e.g., about 2-18 mmol/L). Normal values of direct bilirubin are 0.0-0.2 mg/dl (0-4 mmol/L). Increases in serum bilirubin are indicative of liver disease.

(3) Assays to determine serum protein levels, for example, albumin and the globulins (e.g., alpha, beta, gamma). Normal values for total serum proteins are 6.0-8.0 g/dl (60-80 g/L). A decrease in serum albumin is indicative of liver disease. An increase in globulin is indicative of liver disease.

Other tests include prothrombin time, international normalized ratio, activated clotting time (ACT), partial thromboplastin time (PTT), prothrombin consumption time (PCT), fibrinogen, coagulation factors; alpha-fetoprotein, and alpha-fetoprotein-L3 (percent).

One clinically important type of liver disease is hepatitis. Hepatitis is an inflammation of the liver that can be caused by viruses (e.g., hepatitis virus A, B and C (HAV, HBV, and HCV, respectively), chemicals, drugs, alcohol, inherited diseases, or the patient's own immune system (autoimmune hepatitis). This inflammation can be acute and resolve within a few weeks to months, or chronic, and persist over many years. Chronic hepatitis can persist for decades before causing significant symptoms, such as cirrhosis (scarring and loss of function), liver cancer, or death. Other important examples of the different diseases and disorders encompassed by the term "liver disease" and suitable for treatment or prevention or control using the compositions and methods of the present invention include, but are not limited to amebic liver abscess, biliary atresia, fibrosis, cirrhosis, coccidioidomycosis, delta agent, hepatocellular carcinoma (HCC), alcoholic liver disease, primary biliary cirrhosis, pyogenic liver abscess, Reye's syndrome, sclerosing cholangitis, and Wilson's disease. In some embodiments, the compositions and methods described herein are suitable for the treatment of liver disease characterized by the loss or damage of parenchymal liver cells. In some aspects, the etiology of this can be a local or systemic inflammatory response.

Liver failure occurs when large parts of the liver become damaged and the liver is no longer able to perform its normal physiological function. In some aspects, liver failure can be diagnosed using the above described assays of liver function or by a subject's symptoms. Symptoms that are associated with liver failure include, for example, one or more of the following, nausea, loss of appetite, fatigue, diarrhea, jaundice, abnormal/excessive bleeding (e.g., coagulopathy), swollen abdomen, mental disorientation or confusion (e.g., hepatic encephalopathy), sleepiness, and coma.

Chronic liver failure occurs over months to years and is most commonly caused by viruses (e.g., HBV and HCV), long-term/excessive alcohol consumption, cirrhosis, hemochromatosis, and malnutrition. Acute liver failure is the appearance of severe complications after the first signs of liver disease (e.g., jaundice) and includes a number of conditions, all of which involve severe hepatocyte injury or necrosis. In some embodiments, the compositions and methods described herein are particularly suitable for the treatment of hyperacute, acute, and subacute liver failure, fulminant hepatic failure and late onset fulminant hepatic failure, all of which are referred to herein as "acute liver failure." Common causes for acute liver failure include, for example, viral hepatitis, exposure to certain drugs and toxins (e.g., fluorinated hydrocarbons (e.g., trichloroethylene and tetrachloroethane), amanita phalloides (e.g., commonly found in the "death-cap mushroom"), acetaminophen (paracetamol), halothanes, sulfonamides, henytoins), cardiac-related hepatic ischemia (e.g., myocardial infarction, cardiac arrest, cardiomyopathy, and pulmonary embolism), renal failure, occlusion of hepatic venous outflow (e.g., Budd-Chiari syndrome), Wilson's disease, acute fatty liver of pregnancy, amebic abscesses, and disseminated tuberculosis.

The term "hepatitis" is used to describe a liver condition which implies injury to the liver characterized by the presence of inflammatory cells in the tissue of the organ. The condition can be self-limiting, healing on its own, or can progress to scarring of the liver. Hepatitis is acute when it lasts less than six months and chronic when it persists longer than six months. A group of viruses known as the hepatitis viruses cause most cases of liver damage worldwide. Hepatitis can also be due to toxins (notably alcohol), other infections or from autoimmune process. Hepatitis includes hepatitis from viral infections, including Hepatitis A through E (A, B, C, D and E—more than 95% of viral cause), Herpes simplex, Cytomegalovirus, Epstein-Barr virus, yellow fever virus, adenoviruses; non-viral infections, including toxoplasma, Leptospira, Q fever, rocky mountain spotted fever, alcohol, toxins, including amanita toxin in mushrooms, carbon tetrachloride, asafetida, among others, drugs, including paracetamol, amoxycillin, antituberculosis medicines, minocycline and numerous others as described herein; ischemic hepatitis (circulatory insufficiency); pregnancy; autoimmune conditions, including Systemic Lupus Erythematosus (SLE); and non-alcoholic steatohepatitis.

"Sterile inflammation" is used to describe inflammation of the liver which is triggered by intracellular molecules released from dying cells that have lost integrity of their plasma membrane. This inflammation occurs in the absence of causative agents such as viruses or bacteria and alcohol. A number of intracellular molecules have been identified that can stimulate other cells to produce proinflammatory cytokines and chemokines. Such proinflammatory cellular molecules are thought to function by engaging receptors on cytokine-producing cells. If left untreated, sterile inflammation may progress to non-alcoholic fatty liver disease (NAFLD), non-alcoholic steatohepatitis (NASH) or cirrhosis.

"Non-alcoholic steatohepatitis" or "NASH" is a condition of the liver in which inflammation is caused by a buildup of fat in the liver. NASH is part of a group of liver diseases, known as nonalcoholic fatty liver disease, in which fat builds up in the liver and sometimes causes liver damage that gets worse over time (progressive liver damage). "Non-alcoholic fatty liver disease" (NAFLD) is fatty inflammation of the liver which is not due to excessive alcohol use. It is related to insulin resistance and the metabolic syndrome, obesity, high cholesterol and triglycerides, and diabetes, and may respond to treatments originally developed for other insulin resistant states (e.g. diabetes mellitus type 2), such as weight loss, metformin and thiazolidinediones. Non-alcoholic steatohepatitis (NASH) is the most extreme form of NAFLD, which is regarded as a major cause of cirrhosis of the liver of unknown cause.

Other factors that have been known to contribute to NASH include: surgery that shorten the intestines, the stomach, or both, such as jejunal bypass operation or biliopancreatic diversion; prolonged use of feeding tube or other method of receiving nutrition; certain drugs, including amiodarone, glucocorticoids, synthetic estrogens, and tamoxifen.

NASH is a condition that may get worse over time (called a progressive condition) and can cause scarring (fibrosis) of the liver, which leads to cirrhosis. "Cirrhosis" describes a condition in which liver cells have been replaced by scar tissue. The term "cirrhosis of the liver" or "cirrhosis" is used to describe a chronic liver disease characterized by replacement of liver tissue by fibrous scar tissue as well as regenerative nodules, leading to progressive loss of liver function. Cirrhosis is most commonly caused by fatty liver disease, including NASH, as well as alcoholism and hepatitis B and C, but also may be of unknown cause. Potentially life-threatening complications of cirrhosis are hepatic encephalopathy (confusion and coma) and bleeding from esophageal varices. Cirrhosis has historically been thought to be generally irreversible once it occurs, and historical treatment focused on preventing progression and complications. In advanced stages of cirrhosis, the only option is a liver transplant. Enriched with vitamin D2 mushrooms, or their extracts and methods of the present invention may be used to limit, inhibit, reduce the likelihood or treat cirrhosis of the liver without regard to its etiology.

The biomass, extract or pharmaceutical compositions enriched with vitamin D2 mushrooms and methods of the present invention can be used to delay onset of, protect from, treat, prevent or control chemical liver trauma and hepatotoxicity. "Chemical trauma" or "acute chemical trauma" refers to serious injury which occurs to a patient over a short duration as a consequence of chemical toxicity, including drug-induced toxicity or trauma. Drug-induced acute liver trauma, including acetaminophen-induced acute liver trauma, is acute liver injury which occurs as a result or consequence of exposure to a drug (e.g., drug overdose), especially acetaminophen toxicity. Compounds according to the present invention are useful for reducing the injury to the liver which occurs from physical and chemical trauma, especially including drug-induced (drug overdose) and acetaminophen-induced acute liver trauma.

Hepatotoxocity is chemical liver trauma resulting from a hepatotoxic agent, or hepatotoxicity-inducing bioactive agent. The terms "hepatotoxic agent" and "a hepatotoxicity inducing bioactive agent" are used synonymously in context to describe compounds which often produce hepatotoxicity in patients administered such agents. Examples of hepatoxicity agents include, for example, anaesthetic agents, antiviral agents, anti-retroviral agents (nucleoside reverse transcriptase inhibitors and non-nucleoside reverse transcriptase inhibitors), especially anti-HIV agents, anticancer agents, organ transplant drugs (cyclosporin, tacrolimus, OKT3), antimicrobial agents (anti-TB, anti-fungal, antibiotics), anti-diabetes drugs, vitamin A derivatives, steroidal agents, especially including oral contraceptives, anabolic steroids, androgens, non-steroidal anti-inflammatory agents, anti-depressants (especially tricyclic antidepressants) glucocorticoids, natural products and herbal and alternative remedies, especially including St. John's wort.

Hepatotoxicity may manifest as triglyceride accumulation which leads to either small droplet (microvesicular) or large droplet (macrovesicular) fatty liver. There is a separate type of steatosis where phospholipid accumulation leads to a pattern similar to the diseases with inherited phospholipid metabolism defects (e.g. Tay-Sachs disease).

The biomass, extract or pharmaceutical compositions enriched with vitamin D2 mushrooms, or their extracts and methods of the present invention can be used to delay onset of, protect from, treat, prevent or control chronic liver disease. Chronic liver disease is marked by the gradual destruction of liver tissue over time. Several liver diseases fall under this category, including cirrhosis and fibrosis, the latter of which is often the precursor to cirrhosis. Cirrhosis is the result of acute and chronic liver disease and is characterized by the replacement of liver tissue by fibrotic scar tissue and regenerative nodules leading to a progressive loss of liver function. Fibrosis and nodular regeneration results in the loss of the normal microscopic lobular architecture of the liver. Fibrosis represents the growth of scar tissue resulting from, for example, infection, inflammation, injury, and even healing. Over time, the fibrotic scar tissue slowly replaces the normal functioning liver tissue resulting in a decreasing amount of blood flow to the liver leaving the liver incapable of fully processing nutrients, hormones, drugs, and poisons that are found in the bloodstream. More common causes of cirrhosis include alcoholism, hepatitis C viral infections, ingestion of toxins, and fatty liver, but many other possible causes also exist. Chronic hepatitis C virus (HCV) infection and non-alcoholic steatohepatitis (NASH) are the two major causes of chronic liver disease in the United States estimated to affect between 3-5 million people. A rising concern is the continuously increasing number of U.S. citizens, currently numbering over 30 million, with obesity and metabolic syndrome that have non-alcoholic fatty liver disease (NAFLD) with approximately 10% who will eventually develop NASH. Other bodily complications are a consequence of a loss of liver function. The most common complication of cirrhosis is a condition known as ascites, an accumulation of fluid in the peritoneal cavity, which can lead to an increased risk of spontaneous bacterial peritonitis possibly resulting in the premature death of the patient.

In certain embodiments, the immune-related or inflammatory related disease, disorder or condition is acute or chronic liver disease including alcohol and drug mediated liver disease.

In certain embodiments, the biomass, extract or pharmaceutical composition is used by administering it once, twice, three times/day or more.

In yet an additional aspect, the present invention provides a method for delaying onset of, treating, ameliorating or protecting from an immune-related or inflammatory related disease, disorder or condition in a mammalian subject, said method comprising administering to said subject a therapeutically effective amount of the biomass, the extract, or the pharmaceutical composition as defined herein.

In still a further aspect, the present invention provides the biomass, the extract, or the pharmaceutical composition as defined herein for use in the manufacture of a medicament for delaying onset of, treating, ameliorating or protecting from an immune-related or inflammatory related disease, disorder or condition.

In certain embodiments, the use or method of the present invention relates to a fungal derivative administered alone or in combination with other active ingredient/s that improve the therapeutic effect, whether administered in combination, serially or simultaneously.

The term "treating" as used herein refers in general to means of obtaining a desired physiological effect. The effect may be therapeutic in terms of partially or completely curing a disease and/or symptoms attributed to the disease.

As used herein, the terms "subject" or "individual" or "animal" or "patient" or "mammal," refers to any subject, particularly a mammalian subject, for whom diagnosis, prognosis, or therapy is desired, for example, a human.

The terms "effective amount" or "sufficient amount" mean an amount necessary to achieve a selected result. The "effective treatment amount" is determined by the severity of the disease in conjunction with the preventive or therapeutic objectives, the route of administration and the patient's general condition (age, sex, weight and other considerations known to the attending physician).

It should be appreciated that the delaying of the onset of an immune-related or inflammatory related disease, disorder or condition comprises the administration of a prophylactically effective amount of the biomass, extract or pharmaceutical composition of the invention or of the active ingredients comprised within such composition, to a person at risk of developing a disease.

The term "protecting from an immune-related or inflammatory related disease, disorder or condition" as used herein refers to prevention of the development of the immune-related or inflammatory related disease, disorder or condition.

The term "prophylactically effective amount" is intended to mean the amount of a pharmaceutical combined composition that will delay the onset of, prevent or reduce the risk of occurrence of the biological or medical event that is sought to be prevented in a tissue, a system, animal or human by a researcher, veterinarian, medical doctor or other clinician.

As used herein, the term "disorder" refers to a condition in which there is a disturbance of normal functioning. A "disease" is any abnormal condition of the body or mind that causes discomfort, dysfunction, or distress to the person affected or those in contact with the person.

Sometimes the term is used broadly to include injuries, disabilities, syndromes, symptoms, deviant behaviors, and atypical variations of structure and function, while in other contexts these may be considered distinguishable categories. The term "condition" as used herein refers to a state of health considered normal or healthy but nevertheless posing implications for the provision of health care.

In still a further aspect, the present invention is directed to a kit for use in delaying onset of, treating, ameliorating or protecting from an immune-related or inflammatory-related disease, disorder or condition, said kit comprising: (a) a biomass of an edible fungus; (b) an extract obtained from an edible fungus; or (c) a composition comprising an extract obtained from an edible fungus; (d) vitamin D2; and (e) a leaflet with instructions for administration of a combination of (a), (b) or (c) and (d).

In certain embodiments, the edible fungus of (a), (b), and (c) is an untreated edible fungus, which has for example, not been irradiated with UVB. In certain embodiments, the combination of (a), (b) or (c) and (d) comprises vitamin D2 at level that is two to 100 times, or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 times, higher than the level of vitamin D2 in the same amount of (a), (b) or (c).

The invention further relates to a process for the production of a fungal derivative for use in delaying onset of, treating, ameliorating or protecting from an immune-related or inflammatory related disease, disorder or condition in a subject in need thereof, comprising the steps of fungi (mushrooms) enrichment with vitamin D2.

(a) Fungi cultivation: (1) in a liquid medium (submerged culture) under suitable conditions for mycelium development; or (2) in solid state fermentation conditions for fruit body development;
(b) Enhancement of vitamin D2 content in the harvested fungi, by UVB light pulses;
(c) filtering the fungal mycelium or harvesting the fruit bodies;
(d) drying the live/fresh mycelium or fruit bodies using air, or lyophilization (freeze drying); optionally
(e) producing powders of fresh, dried or freeze dried mycelium or fruiting bodies; optionally
(f) extracting polysaccharides or proteins from fresh, dried or freeze dried mycelium or fruiting bodies; and optionally
(g) admixing the powders or extracts of (e) or the polysaccharides or proteins of (f) with a suitable pharmaceutical carrier forming a pharmaceutical composition.

Without being bound by any theory, the inventors speculate that different fungal preparations exert their beneficial effect upon immune-related disorders through induction of systemic tolerance towards disease associated antigens. The effect of these fungal preparations on lymphocyte sequestration in the liver of both diseased and healthy animals have led the inventors to the hypothesis that fungi acts in a manner which is irrespective of disease induction, as a true immune modulator whose activity is more pronounced in disease states.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

For purposes of clarity, and in no way limiting the scope of the teachings, unless otherwise indicated, all numbers expressing quantities, percentages or proportions, and other numerical values recited herein, should be interpreted as being preceded in all instances by the term "about." Accordingly, the numerical parameters recited in the present specification are approximations that may vary depending on the desired outcome. For example, each numerical parameter may be construed in light of the number of reported significant digits and by applying ordinary rounding techniques.

The term "about" as used herein means that values of 10% or less above or below the indicated values are also included.

The invention will now be illustrated by the following non-limiting examples.

EXAMPLES

Material and Methods
Animals.

Male C57BL/6 mice (11-12 weeks old) were obtained from Harlan Laboratories (Jerusalem, Israel) and maintained in the Animal Core of the Hadassah-Hebrew University Medical School. Mice were administered standard laboratory chow and water ad libitum and kept in a 12 hour light/dark cycle. Animal experiments were carried out according to the guidelines of the Hebrew University-Hadassah Institutional Committee for Care and Use of Laboratory Animals and with the committee's approval.

*Lentinula edodes*
Source:

Mushroom spawn (*Lentinula edodes* 4087) used in this study was purchased from Sylvan (France).

Solid State Fermentation.

Mushrooms were cultivated on a 1:1 mixture of cotton and wheat straws. The straws were oven dried at 60° C. for 24 h and milled to 1-3 cm particle size. The straw mixture was wetted to 70% water content and packed into 4 kg polypropylene bags featuring a microporous filter. The bags were steam sterilized at 100° C. for 2 h, then cooled to 25° C. for inoculation with 2% spawn w/w. The culture was incubated at 25° C. for 30 days. For fruiting, the temperature was reduced to 16° C. with a relative humidity of 90%, 12 h daily light and air $CO_2$ concentration of 800-600 ppm. Post harvested fruit bodies were cooled to 3° C., during 20 minutes. The cooled fruit bodies were separated to two portions. One portion was cooled to −18° C. and then freeze dried and milled, to a powder of, smaller than 1.0 mm particles.

Preparation of Vitamin D Enriched Biomass.

One portion obtained from the solid state fermentation was exposed to three pulses of UVB light, by Xenon RC-847 System. The irradiated fruit bodies were cooled to −18° C. and then freeze dried and milled, to a powder of, smaller than 1.0 mm particles. Vitamin D2 contents (on dry weight basis) were measured by HPLC (Bactochem labs, Israel).

Mushroom Composition:

150 mg freeze-dried mushroom extract was weighed and transferred to 2 ml eppendorf tube.

1.5 ml of Olive Oil was added and the mixture was homogenized at maximum speed for 20 min (10+10) using a standard household blender. 5 mg freeze-dried mushroom was added to the same tube and homogenized at maximum speed for an additional 10 min.

Vitamin D.

Vitamin D was diluted in saline to obtain the desired concentration before administration.

Induction of ConA Hepatitis.

Concanavalin A (ConA, MP Biomedicals, USA) was dissolved in 50 mM Tris pH 7, 150 mM NaCl, 4 mM $CaCl_2$ and was injected into the tail vein at a dose of 500 μg/mouse (15 mg/kg) in the first experiment, and 400 μg/mouse in the second experiment. Mice were sacrificed 16 hours following ConA injection. Blood and liver tissue were collected for further analysis Experimental Groups.

Two consecutive experiments were conducted. In the first study, 4 groups of mice were studied (n=5-6 mice/group). Mice in control group were treated 2 hours before ConA injection with DDW (di distilled water). The first treated group received vitamin D oral supplement (1 IU of vitamin D in saline) twice daily for 3 days prior to Concanavalin A-induced immune liver damage. The second treated group was treated orally with crude freeze-dried biomass derived from *Lentinula edodes* (LE) edible mushrooms (7.5 mg of mushrooms) at the same timing and frequency, while the third treated group was treated with vitamin D enriched LE (7.5 mg of freeze-dried mushrooms containing 1.125 IU of vitamin D). In a subsequent study, four groups of mice (n=5-7 mice/group) were treated by the same protocol detailed above, but the frequency of the oral treatment was increased from two to three times daily.

Assessment of the Effect of Treatment on Liver Damage.
Liver Enzymes.

Serum was obtained from individual mice after sacrifice. The serum aspartate aminotransferase (AST) and alanine aminotransferase (ALT) levels were determined with an automatic analyzer.

Histological Examination of the Liver.

Paraffin-embedded liver sections were prepared from each mouse. The livers were cut into 4-5 μm thin slices and stained with hematoxylin-eosin (H&E). Slides were scored to assess the extent of liver damage using a previously described method [Margalit M, Ghazala S A, Alper R, et al. Glucocerebroside treatment ameliorates ConA hepatitis by inhibition of NKT lymphocytes. Am J Physiol Gastrointest Liver Physiol 2005; 289:G917-25; Massaguer A, Perez-Del-Pulgar S, Engel P, et al. Concanavalin-A-induced liver injury is severely impaired in mice deficient in P-selectin. J Leukoc Biol 2002; 72:262-70].

Measurement of Serum IFN-γ:

Serum IFN-γ levels were measured using a commercially available "sandwich" ELISA kit (Quantikine, R&D Systems, MN, USA).

Statistical Analysis:

Statistical analysis was performed using the Student's t-test. A p value less than 0.05 was considered significant.

Example 1: Effect of Ultraviolet Light Irradiation on Vitamin D Content in the Mushrooms Extracts Table 1 shows that exposure to ultraviolet light increases the average vitamin D2 content in the dry mushrooms powder from 64 to 126 IU/gr in the case of *Lentinula edodes* and from 49 to 148 in the case of *Pleurotus ostreatus*. Table 2 shows that mushrooms grown in the dark have undetectable levels of vitamin D2 prior to UV irradiation and about 70 μg/gr (2800 IU/gr) vitamin D2 after UV irradiation.

TABLE 1

Effect of ultraviolet B radiation on vitamin D concentrations in mushrooms extracts.

| Extract | name | UV | IU/gr | average |
|---|---|---|---|---|
| 1 | Lentinula edodes | + | 150.3 | |
| 2 | Lentinula edodes | + | 101.5 | 125.9 |
| 3 | Pleurotus ostreatus | + | 105.4 | |
| 4 | Pleurotus ostreatus | + | 191.6 | 148.3 |
| 5 | Lentinula edodes | − | 63.3 | |
| 6 | Lentinula edodes | − | 65.1 | 64.2 |
| 7 | Pleurotus ostreatus | − | 39.7 | |
| 8 | Pleurotus ostreatus | − | 59 | 49.35 |

TABLE 2

The impact of UVB irradiation on Vitamin D2 content of *Lentinula edodes* (Shiitake) and *Pleurotus ostreatus* (Oyster) mushrooms grown in the dark.

| | Vit. D2 (μg/1 gr DM) | | | |
|---|---|---|---|---|
| | Shiitake (Control) | Shiitake (Rad) | Oyster (Control) | Oyster (Rad) |
| Average | 0 | 68.901 | 0 | 76.5 |
| Std. Dv. | | 7.767 | | 6.488 |

Figure 1:
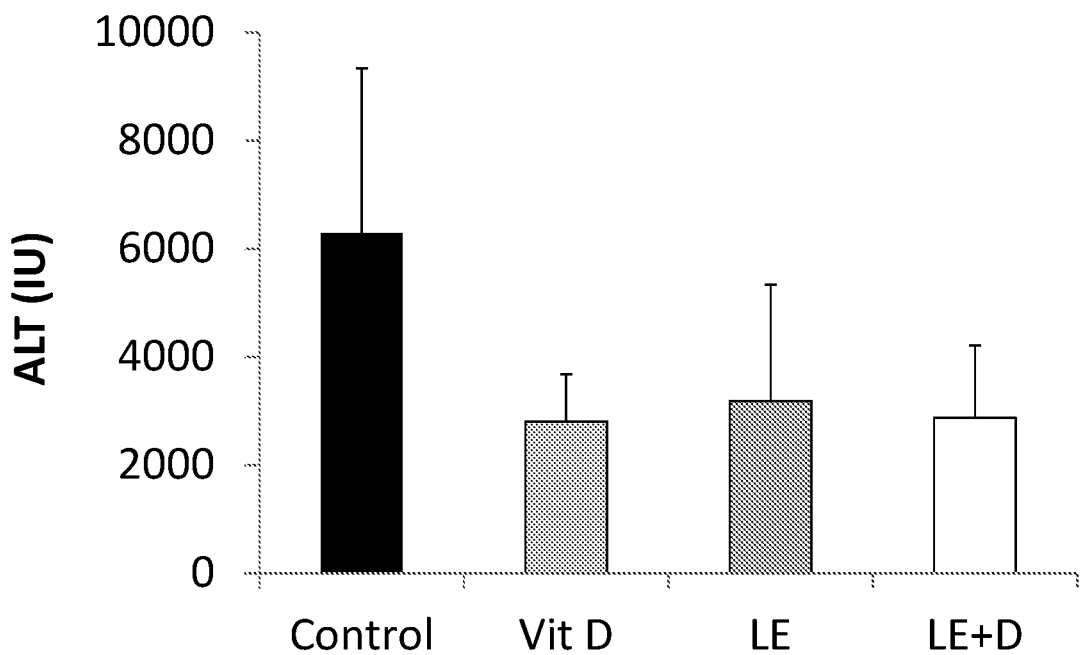
FIG. 1 shows alanine aminotransferase (ALT) serum levels in mice given oral administration (1 IU of vitamin D2) twice daily for 3 days of vitamin D2, *Lentinula edodes* (LE) extract (i.e. biomass), vitamin D2-enriched *Lentinula edodes* (LE+D) extract (i.e. biomass), or double distilled water (DDW; Control) before they were injected with ConA.

Example 2: Effect of Oral Administration of Vitamin D-Enriched Mushroom Extract on Immune Mediated Hepatitis FIG. 1 shows that following feeding of the vitamin D-enriched mushrooms extracts to immune-mediated hepatitis harboring mice, ALT serum levels decreased from 6283 U/L for the control (untreated) group to 2802, 3183 and 2872 U/L for vitamin D, non-enriched and enriched mushrooms extracts treated groups, respectively (p<0.020, <0.036 and <0.022, respectively).

Figure 2:
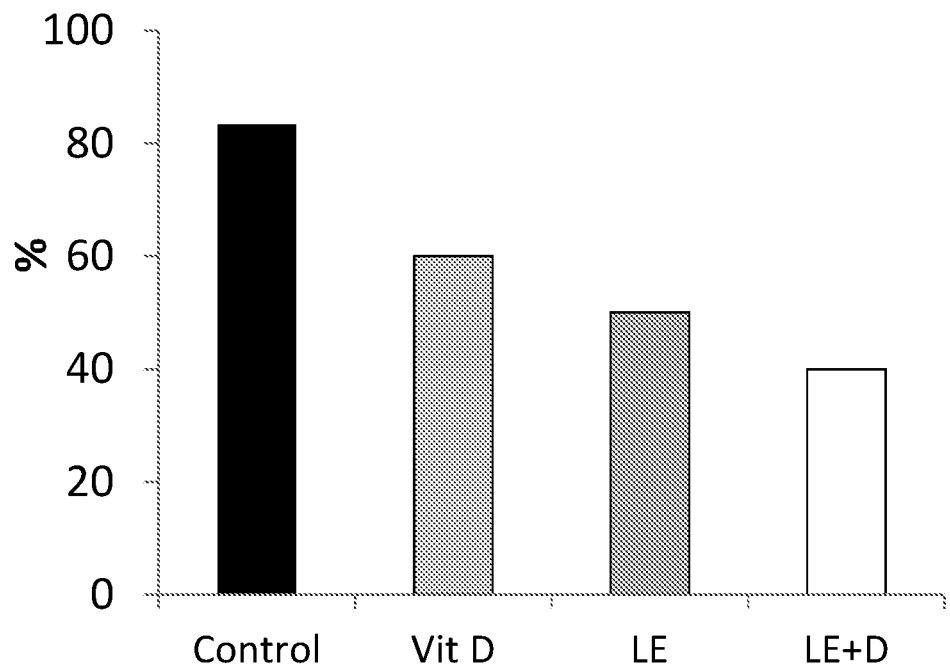
FIG. 2 shows the proportion of mice with severe liver injury (defined as ALT serum level >2611 U/L) in a group of mice given oral administration (1 IU of vitamin D2) twice daily for 3 days of vitamin D2, *Lentinula edodes* (LE) extract (i.e. biomass), vitamin D2-enriched *Lentinula edodes* (LE+D) extract (i.e. biomass, or double distilled water (DDW; Control) before they were injected with ConA.

FIG. 2 shows that the proportion of severe liver injury (defined as ALT>2611 U/L) was decreased from 83% in the control group to 60%, 50% and 40% at the Vitamin D, non-enriched and enriched mushrooms extract treated groups, respectively.

Figure 3:
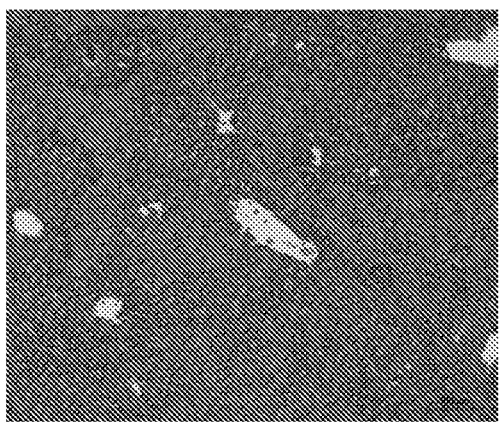
FIG. 3 depicts micrographs of representative slides of liver biopsies revealing a corresponding improvement of the immune mediated liver injury of the first experiment (see results depicted in FIGS. 1 and 2).
Figure 3:
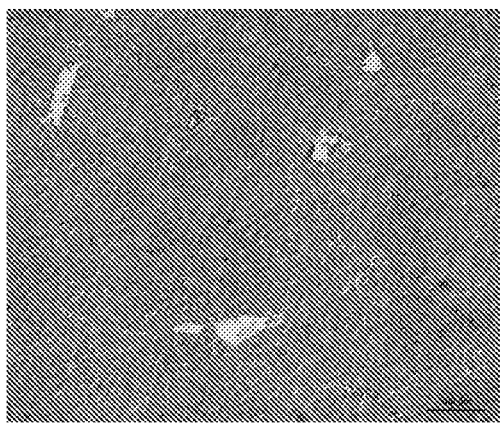
Figure 3:
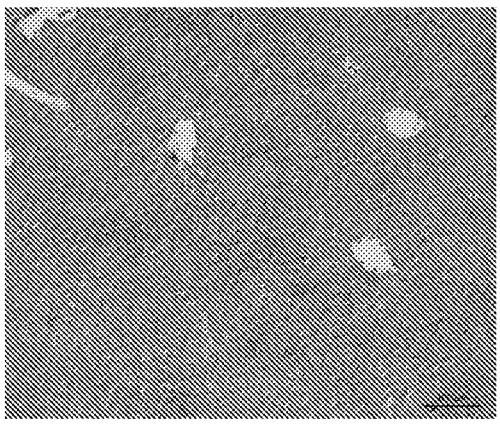
Figure 3:
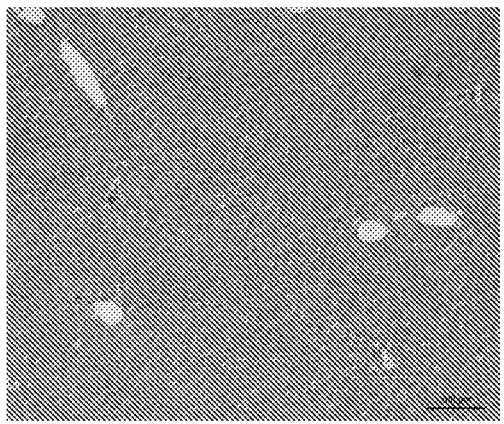

FIG. 3 displays representative pathological sections of liver biopsies showing a corresponding improvement of the immune mediated liver injury of the first experiment, in accordance with the decrease in ALT.

Figure 4:
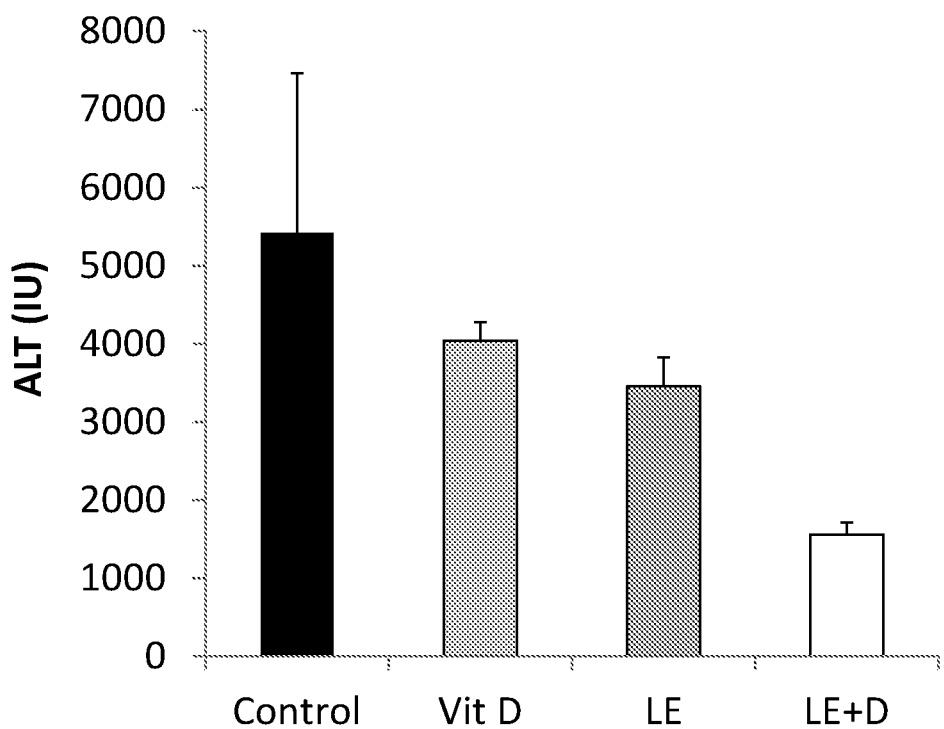
FIG. 4 shows alanine aminotransferase (ALT) serum levels in mice given oral administration (1 IU of vitamin D2) three times daily for 3 days of vitamin D2, *Lentinula edodes* (LE) extract (i.e. biomass), vitamin D2-enriched *Lentinula edodes* (LE+D) extract (i.e. biomass), or double distilled water (DDW; Control) before they were injected with ConA.

Example 3: A Synergistic Effect of Vitamin D with the Mushrooms Extract on Alleviation of Immune Mediated Hepatitis FIG. 4 shows that following feeding of the vitamin D-enriched mushrooms extracts to immune-mediated hepatitis harboring mice in the second study, ALT serum levels decreased from 5423 U/L for the control (untreated) group to 4040, 3455 and 1561 U/L for vitamin D, non-enriched and enriched mushrooms extracts treated groups, respectively (p<0.103, <0.049 and <0.007, respectively).

Figure 5:
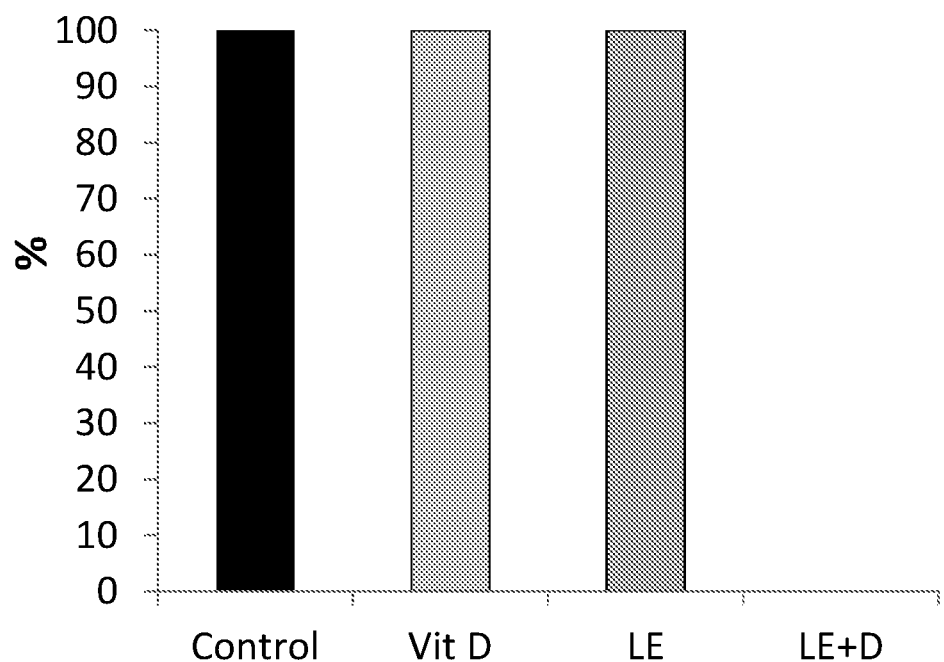
FIG. 5. shows the proportion of mice with severe liver injury (defined as ALT serum level >2600 U/L) in a group of mice given oral administration (1 IU of vitamin D2) three times daily for 3 days of vitamin D2, *Lentinula edodes* (LE) extract (i.e. biomass), vitamin D2-enriched *Lentinula edodes* (LE+D) extract (i.e. biomass), or double distilled water (DDW; Control) before they were injected with ConA.

FIG. 5 shows that the proportion of severe liver injury (defined as ALT >2000 U/L) was 100% at the first three groups (untreated, vitamin D and non-enriched mushrooms extract), but was dramatically decreased to 0% at the enriched mushrooms extract treated group, demonstrating the synergistic effect of the two different treatments, from the second experiment. A similar decrease was noted when comparing the proportion of severe liver injury by AST levers (defined as AST>2000 U/L), 100% at the first three groups and 14.3% at the fourth group (Data not shown).

Example 4: Extracts from *Grifola Frondosa* and *Flammulina Velutipes* Promote Intrahepatic NKT Cells and Ameliorate Immune-Mediated Colitis in Mice Natural killer T (NKT) cells are a subset of regulatory lymphocytes that are abundant in the liver. The liver plays a role in peripheral tolerance induction by promoting this subset of cells and trapping CD8 activated lymphocytes. This study determined the effect of three different mushroom preparations on intrahepatic NKT cells and on colonic inflammation in a murine model of immune-mediated colitis.

Methods

Animals.

Normal inbred 2- to 4-month-old C57BL/6 male mice were obtained from Harlan Laboratories and housed in the Animal Core of the Hadassah-Hebrew University Medical School. Mice were maintained on standard laboratory chow and kept on a 12-hour light/dark cycle. All experiments were performed in accordance with guidelines from the institute's ethical committee for animal handling and were in compliance with the Principles of Laboratory and Animal Regulations Established by the National Society of Medical Research.

Experimental Design.

Three experiments were conducted, one with each of the three mushroom preparations. Each experiment involved four groups of mice (Groups A, B, C, and D) consisting of 10 animals each. Colitis was induced by TNBS administration in Group A and B mice. Group A mice were fed one of the mushroom preparations (50 μg/mouse; 2.5 mg/kg body weight) starting 2 days before induction of colitis by TNBS (day −2) until 9 days after induction (day 9). The first mushroom preparation was powdered fruiting bodies from *L. edodes*, the second and third preparations were extracts from *G. frondosa* or *F. velutipes*, respectively. Group B mice were fed bovine serum albumin (BSA; 50 μg/mouse). Group C mice, which lacked experimentally induced colitis, were also fed a mushroom preparation from the beginning of the experiment (day 0) until day 9. Lastly, Group D mice, which also lacked experimentally induced colitis, were fed BSA (50 μg/mouse). All mice were sacrificed on day 10.

*L. edodes* Preparation.

The *L. edodes* mushroom spawn used in this study (*L. edodes* 4087) was purchased from Sylvan (France). Mushrooms were grown on a 1:1 mixture of cotton and wheat straw. The straw was oven-dried at 60° C. for 24 h and milled (final particle size, 1-3 cm). The straw mixture was then wetted with water (70% water content) and packed into 4-kg polyethylene bags with a microporous filter. The bags were steam-sterilized at 100° C. for 2 h, then cooled to 25° C. for inoculation with 2% (w/w) spawn. The culture was incubated at 25° C. for 30 days. For fruiting, the temperature was reduced to 16° C. with a relative humidity of 90%, 12 h daily light, and a $CO_2$ concentration of 800-600 ppm. The fruiting bodies were then oven-dried at 60° C. for 24 h and milled to a 1-mm particle size. This preparation was called 'Shiitake'.

*F. velutipes* and *G. frondosa* Extracts.

The mushroom mother spawn (*F. velutipes* M4622 and *G. frondosa* M9821) was purchased from Mycelia, SacO2, Combiness (Belgium). Stock cultures were maintained on a potato dextrose agar (PDA) slant and subcultured every 1.5 months. The slants were incubated at 25° C. for 7-15 d and then stored at 4° C. For liquid culture, mushrooms were initially grown on PDA medium in a Petri dish and then transferred to liquid culture medium by punching out a 3×10 $mm^2$ piece of the agar plate culture. The culture was grown at 25° C. in 3 l of medium in Erlenmeyer flasks until the mycelia covered the liquid surface. *G. frondosa* was grown in PMP medium (potato malt peptone medium; 2.4% potato dextrose broth plus 1% malt extract and 0.1% peptone) for 17 days. *F. velutipes* was grown in MCM medium (mushroom complete medium; 0.2% yeast extract, 0.2% peptone, 2% glucose, 0.05% $MgSO_4$. $7H_2O$, 0.046% $KH_2PO_4$, and 0.1% $K_2HPO_4$) for 15 days.

To isolate proteins from *F. velutipes*, the mycelium was harvested by membrane filtration following incubation. The mycelium was washed 3 times with distilled water to remove contaminating extracellular polysaccharides, then ground in a mortar with liquid nitrogen, lyophilized, and stored at −20° C. All subsequent steps were carried out at 4° C. The lyophilized mycelium was homogenized in a Waring blender and extracted overnight with 0.15 M NaCl (1 g/13 ml). The homogenate was centrifuged at 8000 rpm for 20 min, and the supernatant was filtered through glass wool. Soluble proteins in the supernatant were precipitated by adding ammonium sulphate to 80% saturation. After stirring overnight, the precipitate was collected by centrifugation at 20,000×g for 30 min. The pellet was dialyzed with Spectra/Por 3 (MW cut-off, 3.5 kDa) against 10 mM PBS for more than 40 h with at least four changes of dialysis solution. The dialysate was centrifuged (20,000×g for 10 min) to remove denaturated proteins and then filtered through a 0.2-µm membrane filter and lyophilized. These extracted proteins were termed 'FV' and were stored at −20° C. until use.

To isolate polysaccharides from *G. frondosa*, mycelium was harvested by membrane filtration following incubation. The mycelium was washed 3 times with distilled water to remove contaminating extracellular polysaccharides, then ground in a mortar with liquid nitrogen, lyophilized, and stored at −20° C. Lyophilized mycelium was extracted with 120° C. distilled water (1 g/100 ml) for 20 min. The extract was cooled and 2 volumes of cold ethanol were added. The mix was stirred vigorously and then allowed to precipitate overnight at 4° C. The precipitated polysaccharides were collected by centrifugation (8000 rpm for 20 min), dissolved in distilled water, and re-precipitated with 2 volumes of cold ethanol (using the same conditions as noted above). The re-precipitated polysaccharides were again centrifuged at 8000 rpm for 20 min, and the supernatant was discarded. The precipitate was dialyzed with Spectra/Por 3 (MW cut-off, 3.5 kDa) against distilled cold water (to remove small compounds) for at least 24 h with 3 or 4 changes of dialysis solution. After dialysis, the sample was lyophilized and the weight of the crude extract of *G. frondosa* polysaccharides was estimated. The extracted polysaccharides were termed 'GF' and the sample was stored at −20° C. until use.

Determination of Extract Composition.

To determine the total carbohydrate content of GF, we used the phenol-sulphuric acid method described by [Fu and Robyt J F. Prep Biochem 1990; 20:93-106] with some modifications. Aliquots (25-µl) of the GF solution and of glucose standards were placed in triplicate in a 96-well plate, and 25 µl of 5% (w/v) phenol were added. The standards were 0 (distilled water blank), 10, 30, 50, 70, and 90 µg $ml^{-1}$ glucose. After loading samples, the plate was vortexed for 30 s, placed on crushed ice, and 125 µl of concentrated $H_2SO_4$ was added to each well. The plate was mixed for 30 s, sealed in a plastic zipper bag, and warmed in a water bath at 80° C. for 30 min. Each plate was read with a Multiskan Spectrum spectrophotometer (Thermolab Systems, Vantaa, Finland) at 490 nm. The total carbohydrate concentration of the GF samples was determined by comparing the absorbance of the test sample to a plot to the absorbance of the glucose standards. The protein content of the GF and the VF preparations was determined by a standard micro BCA assay [Smith P K et al., Anal Biochem 1985; 150:76-85].

Experimental Colitis.

Colitis was induced by a single enema of TNBS (Sigma Chemicals Co., St. Louis, Mo., USA). TNBS (50 mg) was dissolved in 20% ethanol (total volume 1 ml) and administered through a rubber catheter 10 cm into the colon via the anus, without bowel preparation. The animals were kept fasting for 24 h prior to the procedure and were anesthetized prior to the enema with Ketalar. After the procedure, the mice were supported in the supine position until recovery from the anesthesia to prevent immediate leakage of the TNBS solution.

Colonic damage was assessed 10 days following colitis induction [Trop S, and Ilan Y. J Clin Immunol 2002; 22:270-280]. Distal colonic tissue (10 cm) was removed using a longitudinal incision and gently washed using saline. The freshly-opened colonic segments were examined by an independent observer blinded to the treatment, who assessed the extent of the mucosal damage. Four macroscopic parameters were graded on a scale from 0 (completely normal) to 4 (most severe): degree of colonic ulceration; intestinal and peritoneal adhesions; wall thickness; and degree of mucosal edema.

For each animal, 6 samples of colonic tissue (from the distal 10-cm segment) were prepared for histological analysis. The tissues were fixed in formaldehyde, sliced into 4-6 mm pieces, dehydrated in ethanol, embedded in paraffin wax, sectioned, and stained with hematoxylin and eosin. The degree of inflammation on microscopic cross-sections of the colon was graded semiquantitatively from 0 to 4: Grade 0, normal with no signs of inflammation; Grade 1, very low level of leukocyte infiltration; Grade 2, low level of leukocyte infiltration; Grade 3, high level of infiltration with high vascular density and bowel wall thickening; and Grade 4, transmural infiltrate with loss of goblet cells, high vascular density, wall thickening, and disruption of normal bowel architecture. Two experienced blinded examiners performed the grading.

Evaluation of the Role of NKT Lymphocytes and the Liver in CD4 Trapping.

Splenocytes and liver lymphocytes were isolated as described previously with the following modifications [Ilan Y et al., Treatment of experimental colitis by oral tolerance induction: a central role for suppressor lymphocytes. Am J Gastroenterol 2000; 95:966-73]. The inferior vena cava was cut above the diaphragm and the liver was flushed with 5 ml of cold PBS until it became pale. The connective tissue and the gallbladder were removed, and livers were placed in a 10-ml dish in cold sterile PBS. Splenocytes and liver lymphocytes were isolated by crushing the livers and spleens through a stainless mesh (size 60 mesh, Sigma Chemical Co., St Louis, Mo.). The cell suspension was placed in a 50-ml tube for 3 min and washed twice with cold PBS (1,250 rpm for 10 min). Cells were re-suspended in PBS, put through a nylon mesh presoaked with PBS, and the unbound cells were collected. These cells were washed twice in 45 ml of PBS. For liver and spleen lymphocyte isolation, 20 ml of histopaque 1077 (Sigma Diagnostics, St Louis, Mo.) were added to cells suspended in 7 ml of PBS in a 50-ml tube. After centrifugation at 1,640 rpm for 15 min at room temperature, cells at the interface were collected in a 50-ml tube and washed twice with ice-cold PBS (1,250 rpm for 10 min). Approximately $1 \times 10^6$ cells/mouse liver were recovered. Viability, as assessed by trypan blue staining, was greater than 95%. Both splenocytes and liver-associated lymphocytes were isolated from all animals in all experimental groups.

Flow Cytometry Analysis.

Following lymphocyte isolation, triplicate samples of $2\text{-}5 \times 10^5$ cells/500 µl PBS were placed in Falcon 2052 tubes, incubated with 4 ml of 1% BSA in PBS for 10 min, and centrifuged at 1400 rpm for 5 min. Cells were resuspended in 10 µl FCS with 1:20 FITC-anti mouse CD3 antibody, 1:20 PE-anti mouse CD4 antibody, 1:20 APC-anti mouse CD8 antibody, or 1:20 FITC-anti mouse NK1.1 antibody (NKR-P1C, Pharmingen, USA), and mixed every 10 min for 30 min. Cells were washed twice with 1% BSA and kept at 4° C. until reading. As a FACS control, we also analyzed cells to which 5 µl of 1% BSA (rather than antibodies) were added. Analytical cell sorting was performed on $1 \times 10^4$ cells from each group with a fluorescence-activated cell sorter (FACSTAR plus, Becton Dickinson, Oxnard, Calif.). Only live cells were counted, and the background fluorescence from non-antibody-treated lymphocytes was subtracted. Gates were set on forward- and side-scatter to exclude dead cells and red blood cells. The data were analyzed by the Consort 30 two-color contour plot (Becton Dickinson) or by the CELLQuest programs.

Results

Characterization of the Mushroom Extracts.

The mycelia of F. velutipes and G. frondosa were obtained by submerged cultivation of these strains using MCM and PMP medium, respectively. Flasks were incubated at 25° C. until mycelia covered the liquid surface. Water-soluble polysaccharides (GF) from G. frondosa and saline-soluble proteins (FV) from F. velutipes were isolated. GF was analyzed by the phenol-sulphuric acid method (to determine polysaccharide content) and by the micro BCA method (to determine protein content). The GF extract comprised 56.8% carbohydrates and 8.4% proteins (Table 3); it is likely that the proteins were bound to polysaccharides, since polysaccharide preparations usually contain traces of protein and nucleic acids, depending on the isolation scheme.

TABLE 3

Mycelial growth and polysaccharide and protein content of GF

| | | | | GF composition | | |
|---|---|---|---|---|---|---|
| Mushroom | Media | Growth (d) | Dry mycelia (g/l) | GF mg/g mycelia | Carbohydrates (%) | Proteins (%) |
| Grifola frondosa | PMP | 17 | 0.95 | 25.79 | 56.8 | 8.4 |

GF, polysaccharide extract from G. frondosa.

F. velutipes gave a higher biomass yield and a low yield of protein crude extract (0.88 mg/g mycelia) (Table 4).

TABLE 4

Mycelial growth and protein content and yield of FV

| Mushroom | Media | Growth (d) | Dry mycelia (g/l) | Proteins (FV) (mg/g mycelia) |
|---|---|---|---|---|
| Flammulina velutipes | MCM | 15 | 3.89 | 0.88 |

FV, protein extract from F. velutipes

Mushroom Preparations Increased the Intrahepatic NKT Cells.

Figure 6:
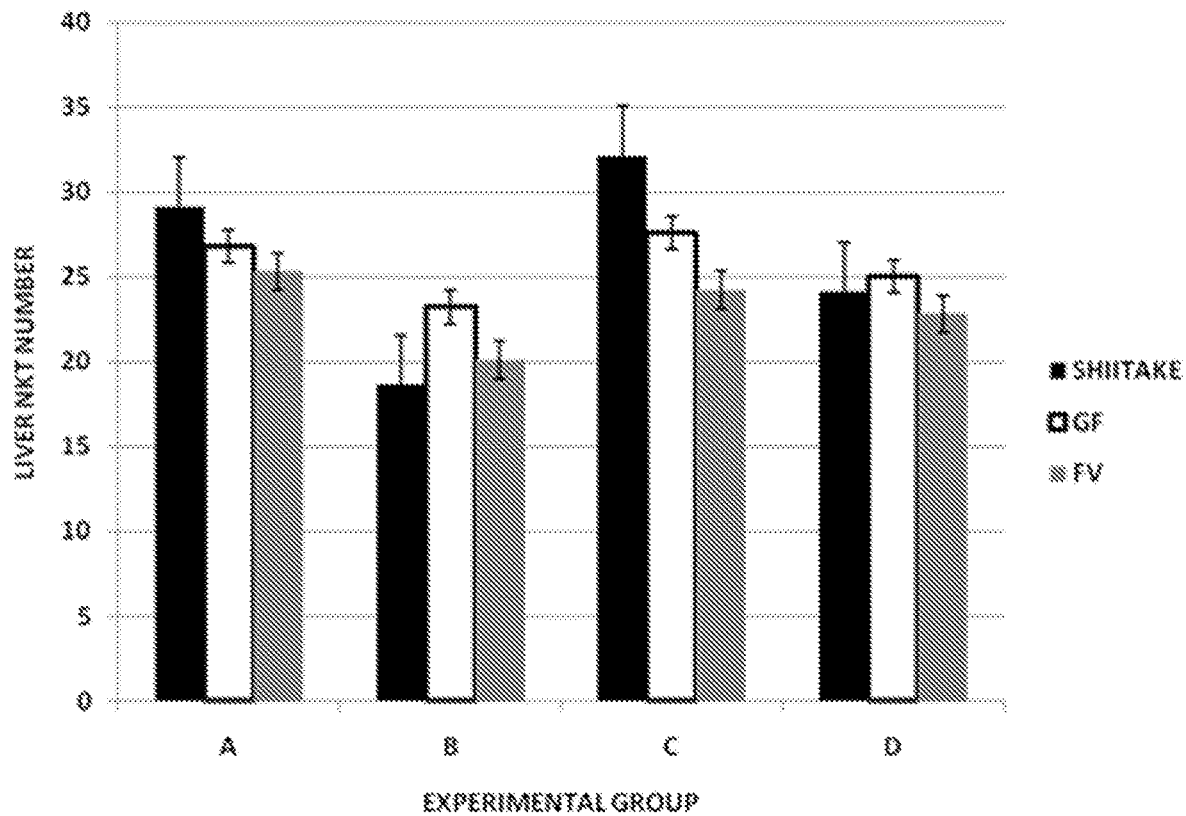
FIG. 6 shows the effect of the mushroom preparations on intrahepatic NKT cells. FACS analysis was performed on liver-derived lymphocytes from mice with (Groups A and B) and without (Groups C and D) experimentally induced colitis. Mice in Groups A and C were fed mushroom preparations as indicated, and mice in Groups B and D were fed BSA. Liver NKT cells increased in Groups A and C compared with mice in Group B and in Group D (control).

The number of intrahepatic NKT cells was determined in all experimental groups. In mice with colitis (Groups A and B), all three mushroom preparations increased the number of hepatic NKT cells. This effect was statistically significant in the groups fed Shiitake and GF but not in the group fed by FV (P<0.005 for Group A vs. Group B, FIG. 6). The greatest increase in NKT cells was observed in mice fed Shiitake. In mice without colitis, i.e. Groups C and D, the mushroom preparations also produced a statistically significant increase in liver NKT cells (P<0.005 in Group C vs. Group D).

To determine whether the increase in intrahepatic NKT cells was due to a systemic increase in NKT cells, the intrasplenic NKT cell count, which reflects the systemic number of NKT cells, was determined and the liver/splenic NKT cell ratio was calculated. This ratio was significantly increased in mice fed with all three mushroom preparations (P<0.005 for Groups A and C vs. B and D, FIG. 7). This finding suggests that the increased number of liver NKT cells was a result of intrahepatic trapping rather than to a systemic increase in NKT cells. The greatest effect was again observed in mice fed the Shiitake preparation.

Mushroom Preparations Increased Intrahepatic CD8 Lymphocyte Trapping.

We used flow cytometry to determine the effect of the mushroom preparations on the distribution of CD4 and CD8 lymphocytes. The intrasplenic (peripheral)/intrahepatic ratio of the CD4/CD8 ratios was then calculated. In mice with induced colitis, all three mushroom preparations markedly increased this ratio (P<0.005 for Group A vs. B, FIG. 8). A non-significant reduction of this ratio was observed in mice without colitis that consumed the mushroom preparations (Group C vs. D, FIG. 3). The increased peripheral/intrahepatic CD4/CD8 ratio suggests CD8 lymphocyte trapping in the liver, which is consistent with systemic tolerance induction.

Increases in Intrahepatic NET and CD8 Lymphocyte Subsets is Associated with an Alleviation of Immune-Mediated Colitis.

The severity of colitis in mice treated with all three mushroom preparations (Group A) was significantly improved compared with Group B mice (P<0.005 for all mushroom preparations, FIG. 9). The greatest reduction in colitis severity was seen with the Shiitake preparation. No signs of colitis were observed in mice in Groups C and D.

All three mushroom preparations also significantly reduced the microscopic scores of inflammation in mice with colitis (P<0.005 for all mushroom preparations, FIG. 10). The greatest reduction in the microscopic score was seen in mice consuming the Shiitake preparation.

The above described experiments are repeated with compositions comprising the different extracts and vitamin D2. Based on the synergistic effect obtained by treatment with biomass of vitamin D2 enriched mushrooms, we expect that the combined composition will provide synergistic effects when compared with the extracts or vitamin D2 alone.

Example 5. Effect of Oral Administration of Vitamin D2-Enriched Mushroom Extract on Immune-Mediated Colitis in Mice Vitamin D2 enriched mushrooms obtained as described in Example 1 are administered to a mice model of Immune-Mediated Colitis and examined as described in Example 4.

The invention claimed is:

1. A method for delaying onset of, treating, ameliorating or protecting from an immune-related or inflammatory related disease, disorder or condition in a mammalian subject, said method comprising administering to said subject a therapeutically effective amount of an extract of an edible fungus or a therapeutically effective amount of a vitamin D2-enriched biomass of an edible fungus, wherein the level of vitamin D2 in said biomass is at least 80 IU/gr; or said method comprising administering to said subject a therapeutically effective amount of vitamin D2-enriched biomass of said edible fungus, wherein vitamin D2 is present in said biomass at a level that is at least about 2 times higher than the level of vitamin D2 in a biomass of said edible fungus that has not been exposed to UVB radiation, wherein said fungus is selected from the group consisting of *Lentinula edodes, Flammulina veluptipes, Pleurotus ostreatus* and *Grifola frondosa*.

2. The method of claim 1, wherein said biomass is obtained from a UVB-treated edible fungus.

3. The method of claim 1, wherein said biomass is obtained from the fruiting body or mycelium of said edible fungus.

4. The method of claim 1, wherein said extract is a solvent-free extract.

5. The method of claim 1, wherein said extract is obtained with a solvent selected from the group consisting of water, saline, steam, an alcohol, an organic solvent, carbon dioxide or combinations thereof.

6. A composition comprising 1) a biomass or extract of an untreated edible fungus and 2) vitamin D2, wherein the level of vitamin D2 is at least 80 IU/gr.

7. The composition of claim 6, wherein at least some of the vitamin D2 originates from a source different from the biomass or extract of the edible fungus.

8. The method of claim 1, wherein said immune-related or inflammatory related disease, disorder or condition is selected from an autoimmune disease, a graft rejection pathology, an inflammatory disease, a nonalcoholic fatty liver disease, hyperlipidemia, atherosclerosis, metabolic syndrome and acute or chronic liver disease.

9. The method of claim 8, wherein said autoimmune disease is selected from inflammatory bowel disease, rheumatoid arthritis, type I diabetes, asthma, acute and chronic graft versus host disease, systemic lupus erythmatosus, scleroderma, multiple sclerosis, and immune mediated hepatitis.

10. The method of claim 9, wherein said autoimmune disease is inflammatory bowel disease selected from the group consisting of ulcerative colitis or Crohn's disease.

11. The method of claim 1, wherein said immune-related or inflammatory related disease, disorder or condition is selected from dyslipoproteinemia, obesity, non-insulin dependent diabetes mellitus (NIDDM), impaired glucose tolerance (IGT), blood coagulability, blood fibrinolysis defects and hypertension and nonalcoholic steatohepatitis (NASH) and fatty liver disease (NAFLD).

12. The method of claim 11, wherein said immune-related or inflammatory related disease, disorder or condition is metabolic syndrome comprising at least two of said immune-related disorders.

13. The method of claim 1, wherein said immune-related or inflammatory related disease, disorder or condition is acute or chronic liver disease including alcohol and drug mediated liver disease.

14. A kit for use in delaying onset of, treating, ameliorating or protecting from an immune-related or inflammatory related disease, disorder or condition, said kit comprising:
(a) a biomass of an edible fungus, an extract obtained from an edible fungus, or a composition comprising an extract obtained from an edible fungus;
(b) vitamin D2; and
(c) a leaflet with instructions for administration of a combination of (a) and (b).

15. A method for delaying onset of, treating, ameliorating or protecting from an autoimmune disease in a mammalian subject, said method comprising administering to said subject a therapeutically effective amount of an extract of an edible fungus or a therapeutically effective amount of a vitamin D2-enriched biomass of an edible fungus, wherein the level of vitamin D2 in said biomass is at least 80 IU/gr; or said method comprising administering to said subject a therapeutically effective amount of vitamin D2-enriched biomass of said edible fungus, wherein vitamin D2 is present in said biomass at a level that is at least about 2 times higher than the level of vitamin D2 in a biomass of said edible fungus that has not been exposed to UVB radiation, wherein said autoimmune disease is selected from the group consisting of inflammatory bowel disease, rheumatoid arthritis, type I diabetes, asthma, acute and chronic graft versus host disease, systemic lupus erythmatosus, scleroderma, multiple sclerosis, and immune mediated hepatitis; and said inflammatory related disease, disorder or condition is selected from the group consisting of dyslipoproteinemia, obesity, non-insulin dependent diabetes mellitus (NIDDM), impaired glucose tolerance (IGT), blood coagulability, blood fibrinolysis defects and hypertension and nonalcoholic steatohepatitis (NASH) fatty liver disease (NAFLD), acute or chronic liver disease including alcohol and drug mediated liver disease.

16. The method of claim 15, wherein said autoimmune disease is inflammatory bowel disease selected from the group consisting of ulcerative colitis or Crohn's disease.

17. The method of claim 15, wherein said inflammatory related disease, disorder or condition is metabolic syndrome comprising at least two of said immune-related disorders.

18. A method for delaying onset of, treating, ameliorating or protecting from an immune-related or inflammatory related disease, disorder or condition in a mammalian subject, said method comprising administering to said subject a therapeutically effective amount of vitamin D2-enriched extract of a biomass of an edible fungus, wherein the level of vitamin D2 in said biomass is at least 80 IU/gr; and wherein said extract is obtained by a solvent free extraction or said extract is obtained with a solvent selected from the group consisting of water, saline, steam, an alcohol, an organic solvent, carbon dioxide or combinations thereof.

* * * * *